(12) United States Patent  
Butler et al.

(10) Patent No.: US 7,731,751 B2
(45) Date of Patent: Jun. 8, 2010

(54) EXPANDABLE SPINAL DEVICES AND METHOD OF INSERTION

(75) Inventors: Michael S. Butler, St. Charles, IL (US); Michael J. Milella, Jr., Schaumberg, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 585 days.

(21) Appl. No.: 11/394,719

(22) Filed: Mar. 31, 2006

(65) Prior Publication Data
US 2006/0224241 A1   Oct. 5, 2006

Related U.S. Application Data

(60) Provisional application No. 60/666,945, filed on Mar. 31, 2005.

(51) Int. Cl.
*A61F 2/44* (2006.01)

(52) U.S. Cl. .................... 623/17.11; 606/279

(58) Field of Classification Search ............... 606/246, 606/248, 249; 623/17.11, 17.12–17.14, 17.15–17.16
See application file for complete search history.

(56) References Cited

U.S. PATENT DOCUMENTS

| | | | | |
|---|---|---|---|---|
| 5,390,683 A * | 2/1995 | Pisharodi | ............... | 623/17.16 |
| 5,658,335 A * | 8/1997 | Allen | ............... | 623/17.16 |
| 5,658,337 A | 8/1997 | Kohrs et al. | | |
| 6,126,689 A * | 10/2000 | Brett | ............... | 623/17.16 |
| 6,176,882 B1 * | 1/2001 | Biedermann et al. | ..... | 623/17.15 |
| 6,375,682 B1 * | 4/2002 | Fleischmann et al. | .... | 623/17.12 |
| 6,409,766 B1 | 6/2002 | Brett | | |
| 6,491,724 B1 | 12/2002 | Ferree | | |
| 6,494,883 B1 | 12/2002 | Ferree | | |
| 6,537,320 B1 | 3/2003 | Michelson | | |
| 6,648,917 B2 * | 11/2003 | Gerbec et al. | ............ | 623/17.11 |
| 6,773,460 B2 | 8/2004 | Jackson | | |
| 7,087,055 B2 * | 8/2006 | Lim et al. | ..................... | 606/99 |
| 2004/0153156 A1 * | 8/2004 | Cohen et al. | ............. | 623/17.13 |
| 2004/0167625 A1 * | 8/2004 | Beyar et al. | ............. | 623/11.11 |
| 2005/0033437 A1 * | 2/2005 | Bao et al. | ................ | 623/17.15 |

(Continued)

FOREIGN PATENT DOCUMENTS

WO   WO 2006/105437 A2   10/2006

OTHER PUBLICATIONS

International Search Report for Application No. PCT/US06/12060, date of mailing Apr. 5, 2007, 1 page.

(Continued)

*Primary Examiner*—Thomas C Barrett
*Assistant Examiner*—Larry E Waggle, Jr.
(74) *Attorney, Agent, or Firm*—Foley & Lardner LLP

(57) ABSTRACT

A device for insertion into a spinal (intervertebral or intravertebral) space is expandable from a first circumference to a second circumference through axial compression of segments of the device, particularly once the device has been properly situated within a vertebral space. The interbody/intravertebral body device is characterized by a plurality of axially stacked, individual segments that are provided on a central insertion and deployment rod. Each segment includes a central plate or body to which are pivotally attached plate or leaf structures. Pivoting of the structures provides a collapsed or unexpanded position of the first circumference and an open or expanded position of the second circumference.

32 Claims, 22 Drawing Sheets

U.S. PATENT DOCUMENTS

2005/0131536 A1* 6/2005 Eisermann et al. ....... 623/17.11
2005/0143827 A1* 6/2005 Globerman et al. ...... 623/17.16
2005/0228391 A1* 10/2005 Levy et al. .................... 606/86
2006/0095136 A1* 5/2006 McLuen .................. 623/23.47
2006/0189999 A1* 8/2006 Zwirkoski .................... 606/90

OTHER PUBLICATIONS

Written Opinion of the International Searching Authority for Application No. PCT/US06/12060, date of mailing Apr. 5, 2007, 3 pages.
International Preliminary Report on Patentability for Application No. PCT/US06/12060, date of completion Jul. 18, 2007, 3 pages.

* cited by examiner

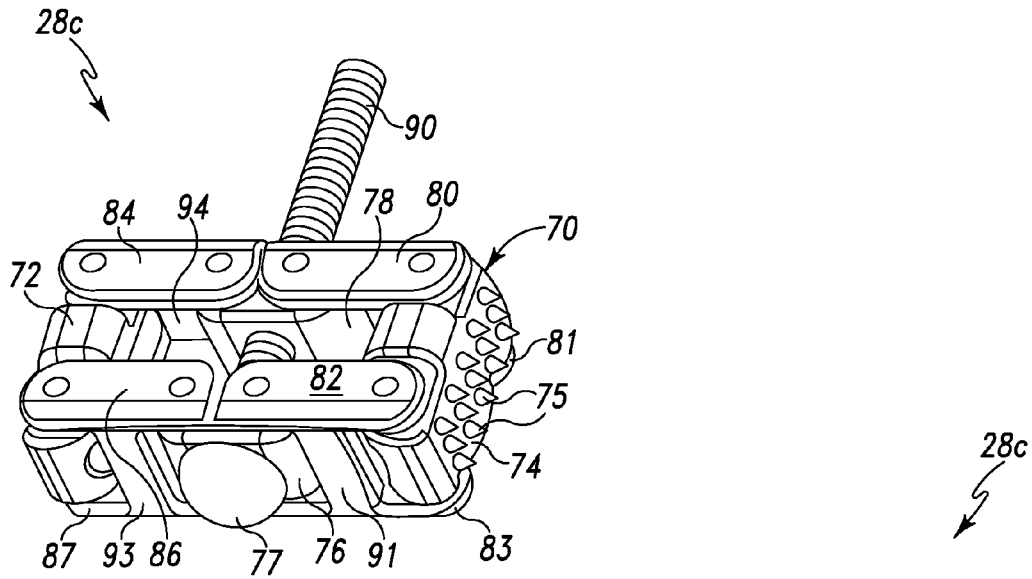
Fig. 11
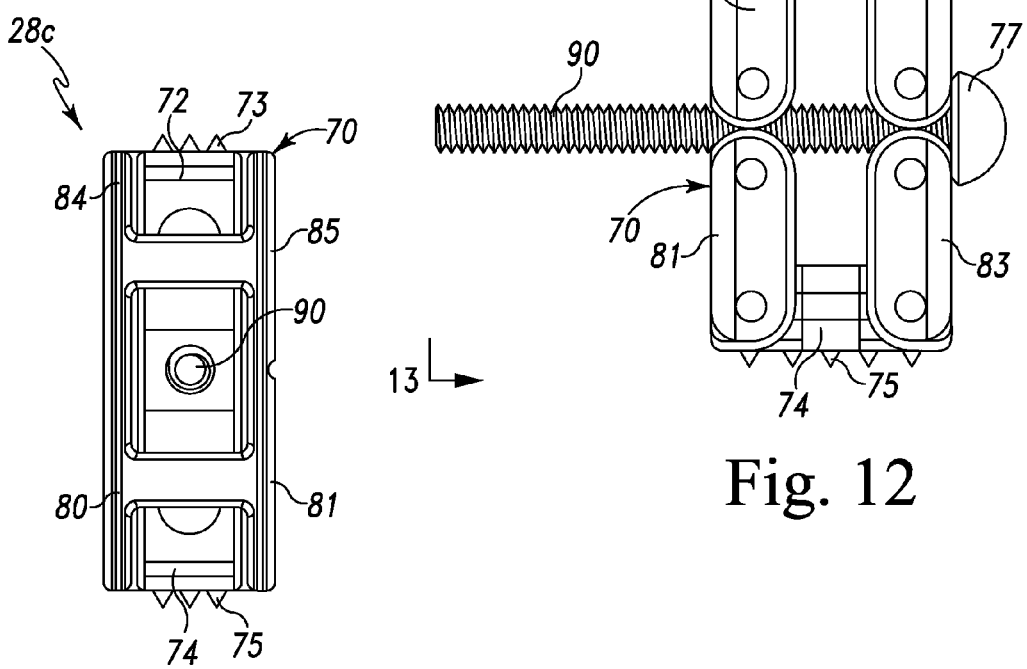
Fig. 12
Fig. 13

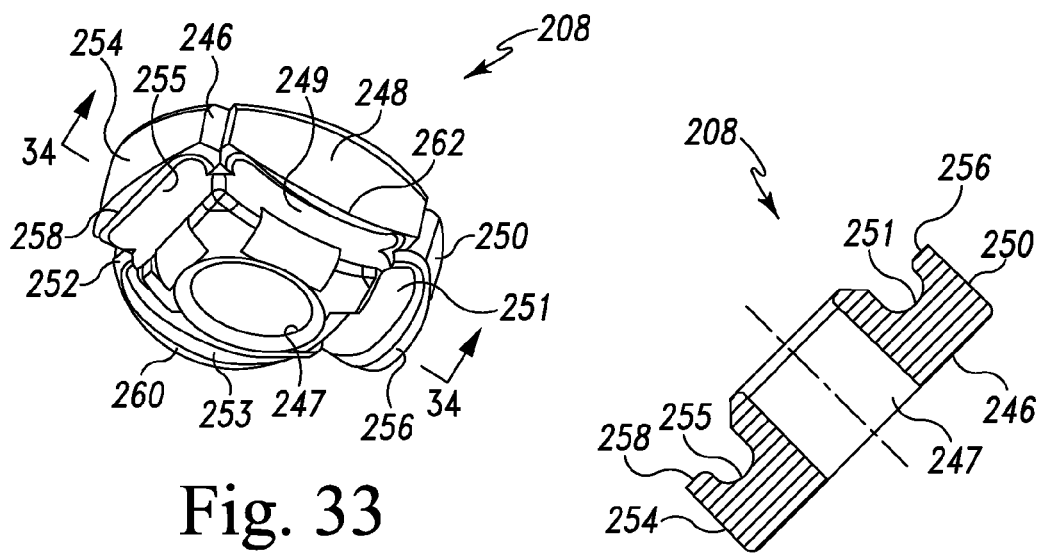
Fig. 33
Fig. 34
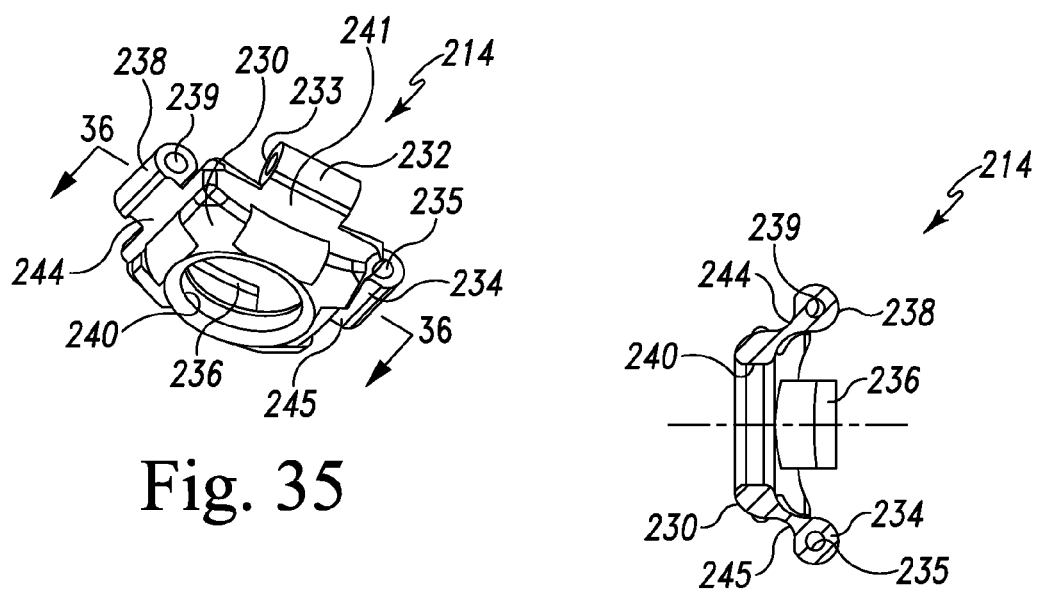
Fig. 35
Fig. 36

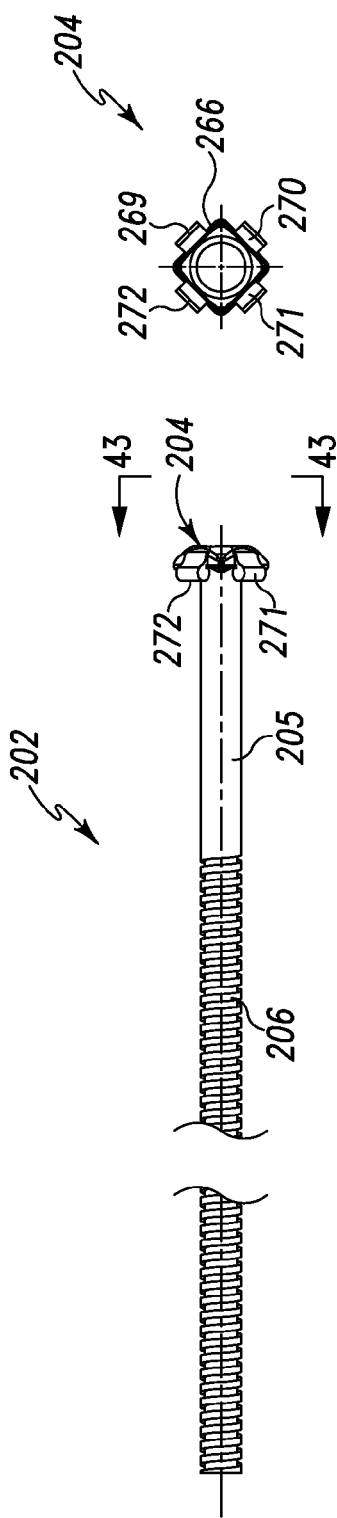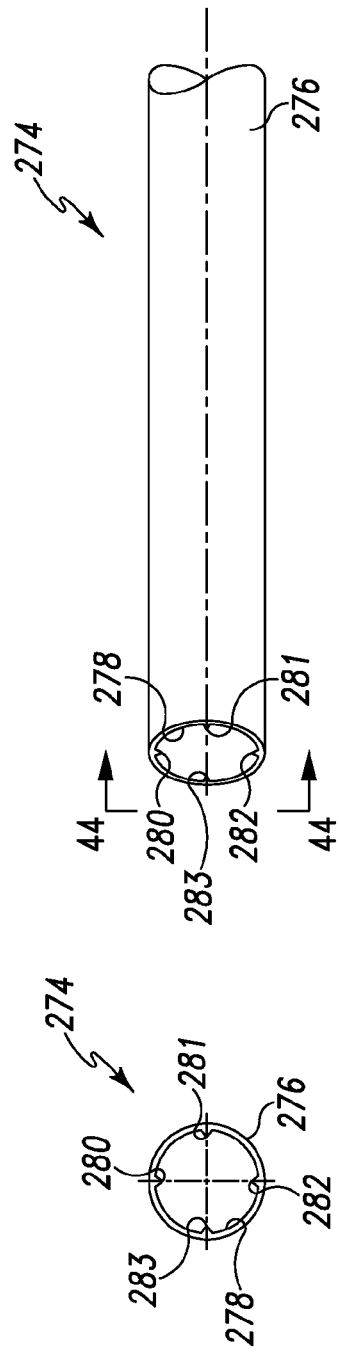
Fig. 42
Fig. 43
Fig. 45
Fig. 44

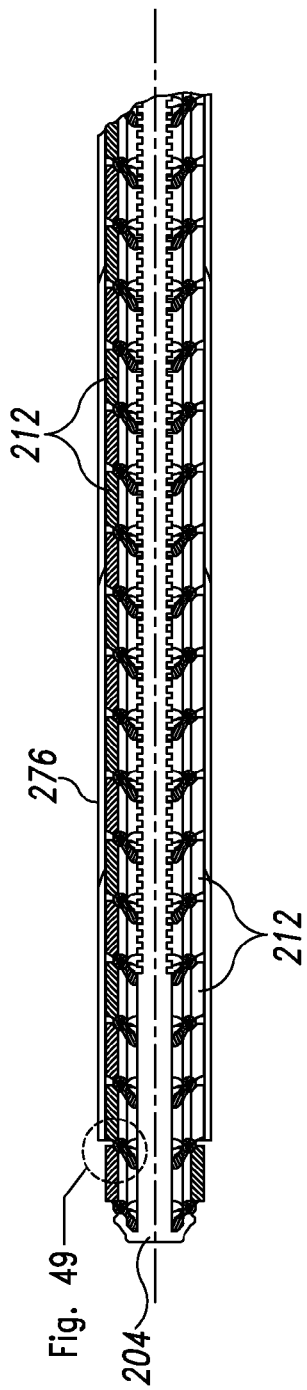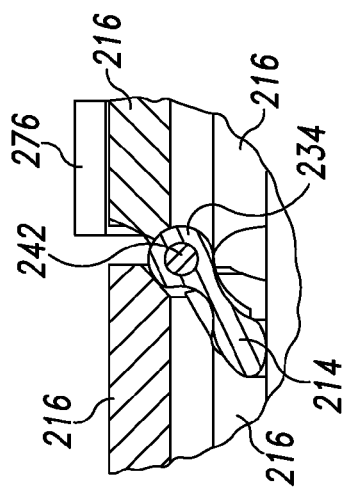

EXPANDABLE SPINAL DEVICES AND METHOD OF INSERTION

CROSS-REFERENCE TO RELATED APPLICATIONS

This patent application claims the benefit of and/or priority to U.S. provisional patent application Ser. No. 60/666,945 filed Mar. 31, 2005, entitled "Dynamic Interbody Stabilization Devices" the entire contents of which is specifically incorporated herein by reference.

FIELD OF THE INVENTION

The present invention relates to spinal interbody and intravertebral body devices and, more particularly, to vertebral interbody and intravertebral devices that are expandable after spinal placement thereof.

BACKGROUND OF THE INVENTION

Fusion cages, as well as other types of bodies and/or devices, are frequently utilized in spinal surgery inside a vertebra (intravertebral) and/or between vertebrae of a patient (interbody). With interbody devices, one or more such spinal bodies are placed between vertebrae to provide support and promote fusion between adjacent vertebrae where such is necessary due to disease, injury, general deterioration or congenital problem. With intravertebral devices, one or more spinal bodies are placed within a vertebra. Spinal devices, such as fusion cages and/or the like, are inserted into a spinal space either anteriorly, posteriorly, laterally or posteriolaterally.

A problem with most spinal interbody and intravertebral devices is that they are static in size. This poses various problems with their use and/or implantation. Particularly, static sized spinal devices are fairly large in order to properly bridge the gap between adjacent vertebrae. This large size does not lend itself to microsurgery, arthroscopic surgery or the like.

A few interbody devices, however, are now being made that are expandable. Expandable interbody devices allow the interbody device to be initially smaller than traditional non-expandable (static) interbody devices such that expandable interbody devices may be more easily inserted or implanted into the vertebral space. Moreover, expandable interbody devices allow the surgeon to set the amount of expansion necessary for the particular patient rather than the static interbody device dictating the spacing.

However, current expandable spinal devices lack strength, reliability and/or simplicity of design.

In view of the above, it is desirable to provide expandable spinal devices that address prior art concerns.

In view of the above, it is desirable to provide expandable spinal interbody devices that address prior art concerns.

In view of the above, it is desirable to provide expandable spinal intravertebral body devices that address prior art concerns.

SUMMARY OF THE INVENTION

The present invention provides expandable spinal interbody and intravertebral body devices for insertion and maintenance between adjacent vertebrae and inside a vertebra of the spine. Particularly, the present invention provides various embodiments of expandable and/or dynamic vertebral interbody and intravertebral body devices that expand from a first radial profile into a second radial profile.

One or more of the present various expandable interbody and intravertebral devices may also provide a dynamization, mobilization or artificial disk platform. One or more of the various dynamic expandable interbody/intravertebral body devices as an artificial disk platform thus allows micro motion of the spine to occur. Additionally, one or more of the present various dynamic expandable interbody/intravertebral devices may function as a fusion device when bone, therapeutic agent or the like is included therein.

In one form, an expandable vertebral interbody/intravertebral body device for insertion into a vertebral space is provided. The interbody/intravertebral body device is expandable from a first circumference (radial profile) to a second circumference (radial profile) through axial compression of segments of the vertebral interbody/intravertebral body device, particularly once the interbody/intravertebral body device has been properly situated within a vertebral space. The interbody/intravertebral body device is characterized by a plurality of axially stacked, individual segments that are provided on a central insertion and deployment rod. Each segment includes a central plate or body to which are pivotally attached plate or leaf structures. Pivoting of the structures provides a collapsed or unexpanded position of the first circumference and an open or expanded position of the second circumference. The vertebral interbody/intravertebral body device may be formed of a bio-compatible radiolucent material. The radial profile of an interbody/intravertebral body device is easily defined by plate or leaf structures of the segments.

BRIEF DESCRIPTION OF THE DRAWINGS

The foregoing and other features of the present invention will become more apparent to one skilled in the art upon also reading the following description of embodiments with reference to the accompanying drawings wherein:

FIG. 11 is a perspective view of the expandable interbody/intravertebral body device of FIG. 7 shown in a post-implant or expanded state;

FIG. 12 is a side view of the expandable interbody/intravertebral body device of FIG. 11;

FIG. 13 is a right side view of the expandable interbody/intravertebral body device of FIG. 12 taken along line 13-13 thereof;

FIG. 33 is a perspective view of an end plate of the expandable interbody/intravertebral body device of FIG. 23;

FIG. 34 is a sectional view of the end plate of FIG. 33 taken along line 34-34 thereof;

FIG. 35 is a perspective view of a deploy plate of the interbody/intravertebral body segment of the expandable interbody/intravertebral body device of FIG. 23;

FIG. 36 is a sectional view of the deploy plate of FIG. 35 taken along line 36-36 thereof;

FIG. 42 is a side view of an implant and deploy rod for use with the expandable interbody/intravertebral body device of FIG. 23;

FIG. 43 is a right side (end) view of the rod of FIG. 42 taken along line 43-43 thereof;

FIG. 44 is an end view of an exemplary insertion and deployment cannula for the various expandable interbody/intravertebral body devices taken along line 44-44 of FIG. 45;

FIG. 45 is a side view of the exemplary insertion and deployment cannula of FIG. 44;

FIG. 48 is a sectional view of FIG. 47 taken along line 48-48 thereof;

FIG. 49 is an enlarged, sectional portion of FIG. 48;

Figure 1:
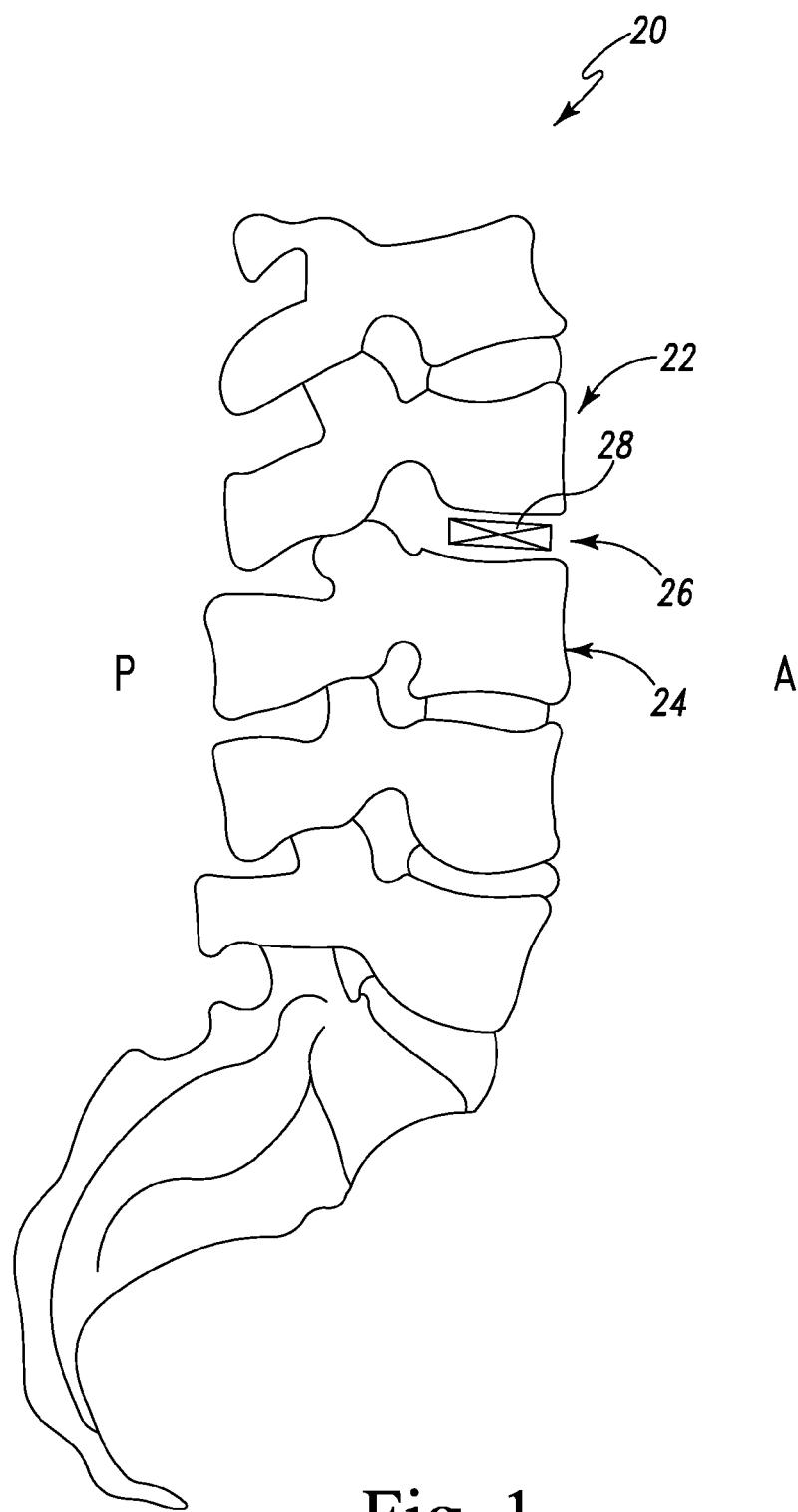
FIG. 1 is a side view of a portion of a human spine illustrating inter-vertebral placement of an expandable interbody/intravertebral body device in accordance with the principles of the present invention.

Corresponding reference characters indicate corresponding parts throughout the several views. Although the drawings represent embodiments of the invention, the drawings are not necessarily to scale and certain features may be exaggerated in order to better illustrate and explain the principles of the present invention. The exemplifications set out herein illustrate several embodiments of the invention, but the exemplifications are not to be construed as limiting the scope of the invention in any manner.

DETAILED DESCRIPTION OF THE INVENTION

The present invention relates to expandable and/or dynamic interbody (between adjacent vertebrae), intravertebral body devices (inside the vertebrae) and/or spinal stabilization devices that may or may not be used as interbody fusion cages or devices, interbody/intravertebral bodies/body stabilization devices and/or the like (collectively hereinafter, spinal device(s)) for providing support, stabilization and/or promoting bone growth between or inside vertebrae that have been destabilized or otherwise due to injury, illness and/or the like. Particularly, the present invention provides various versions of dynamic (expandable and/or expandable and retractable) interbody/intravertebral body devices that are usable in a spinal column of a human. As representative of each one of the various versions of the present invention, FIG. 1 illustrates a representative dynamic spinal body device 28. The spinal body 28 is depicted as implanted or inserted into a human spine of which only a lower portion 20 of the spine is shown. The spinal device 28 is illustrated implanted between adjacent upper and lower vertebrae 22, 24 of the spine portion 20 in FIG. 1 (hence interbody or intervertebral). A spinal device 28 illustrated as body 28f is shown as implanted into a vertebra (hence intravertebral body) in FIGS. 57 and 58. Vertebrae 22 and 24 have portions that face anteriorly ("A", and from the right as viewed in FIG. 1) and portions that face posteriorly ("P", and from the left as viewed in FIG. 1).

Figure 2:
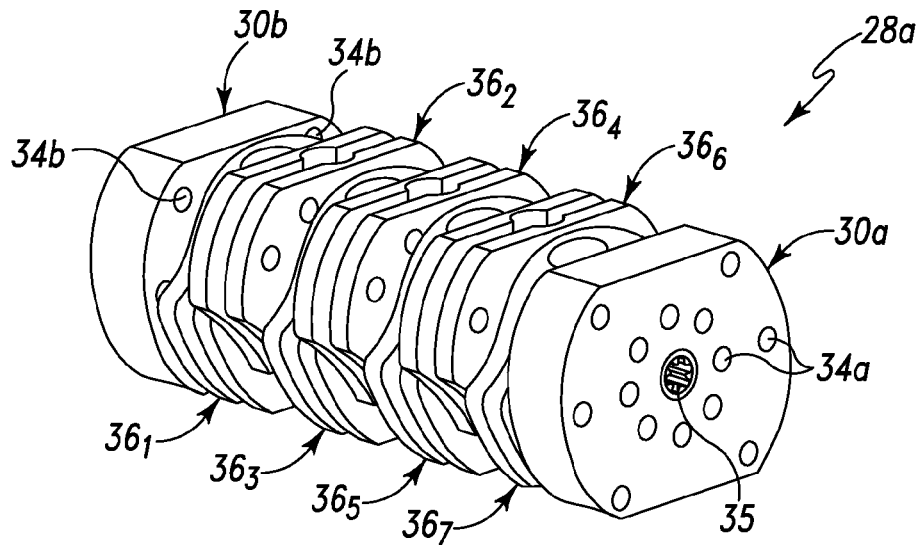
FIG. 2 is a perspective view of an exemplary embodiment of an expandable interbody/intravertebral body device in accordance with the present principles, the expandable interbody/intravertebral body device depicted in a pre-implant or unexpanded state.
Figure 3:
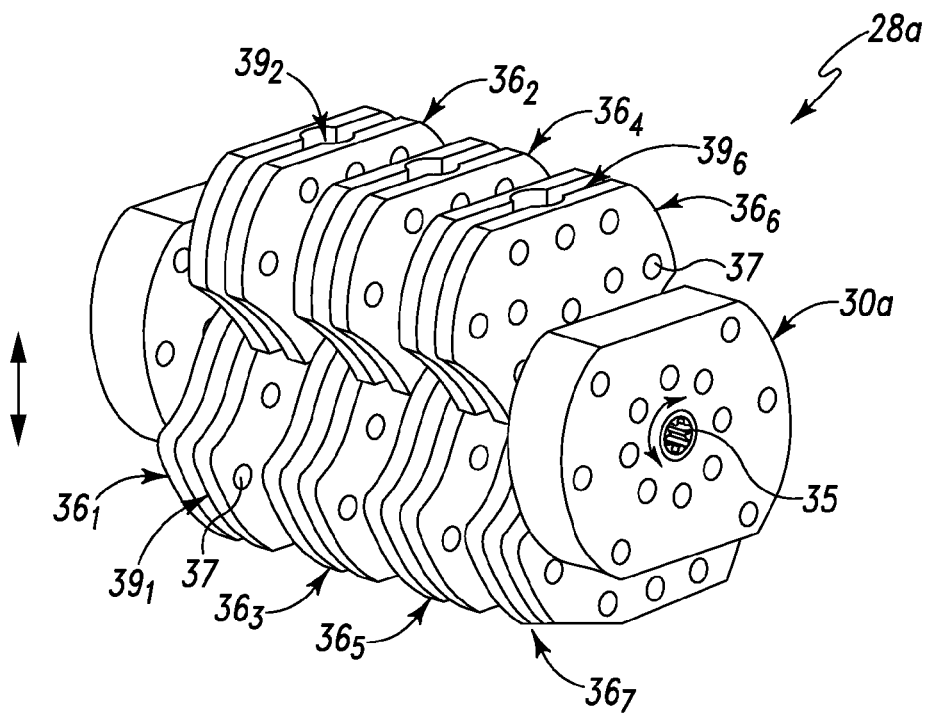
FIG. 3 is a perspective view of the expandable interbody/intravertebral body device of FIG. 2 depicted in a post-implant or expanded state.

Referring to FIGS. 2 and 3, there is depicted an embodiment of an expandable and retractable interbody/intravertebral body device generally designated 28a. FIG. 2 depicts the interbody/intravertebral body device 28a in a fully unexpanded or fully retracted position, while FIG. 3 depicts the interbody/intravertebral body device 28a in a fully expanded or fully un-retracted position. Of course, the interbody/intravertebral body device 28a may be positioned anywhere between the fully expanded to fully retracted positions.

The interbody/intravertebral body device 28a is a posterior (can be inserted in any direction) inserted interbody/intravertebral body device that provides controlled, vertical expansion within the intervertebral space 26 as well as vertical retraction within the intervertebral space 26. The interbody/intravertebral body device 28a includes identical end plates 30a, 30b each having holes or bores 34a, 34b therethrough. A central axis or shaft 35 has ends retained in each end plate 30a, 30b for rotation of the shaft 35. The ends of the shaft 35 are configured to receive a tool for rotation of the shaft and the expansion or retraction of a plurality of plates $36_1$, $36_2$, $36_3$, $36_4$, $36_5$, $36_6$, and $36_7$.

Each one of the plurality of plates 36 includes holes or bores 37. Additionally, each plate 36 is partially bifurcated creating a slot 39 in each plate. The plates 36 are connected to the shaft 35 such that one set of plates $36_1$, $36_3$, $36_5$, and $36_7$ move in one outward direction (expansion) upon shaft rotation in a first direction while another set of plates $36_2$, $36_4$, and $36_6$ move in another (opposite) outward direction (expansion) upon shaft rotation in the first direction. Shaft rotation in a second direction causes both sets of plates to retract. The adjustment of the expansion/retraction of the plates $36_1$, $36_2$, $36_3$, $36_4$, $36_5$, $36_6$, and $36_7$ is done in situ. The interbody/intravertebral body device 28a may also act as an artificial disk allowing movement.

Figure 4:
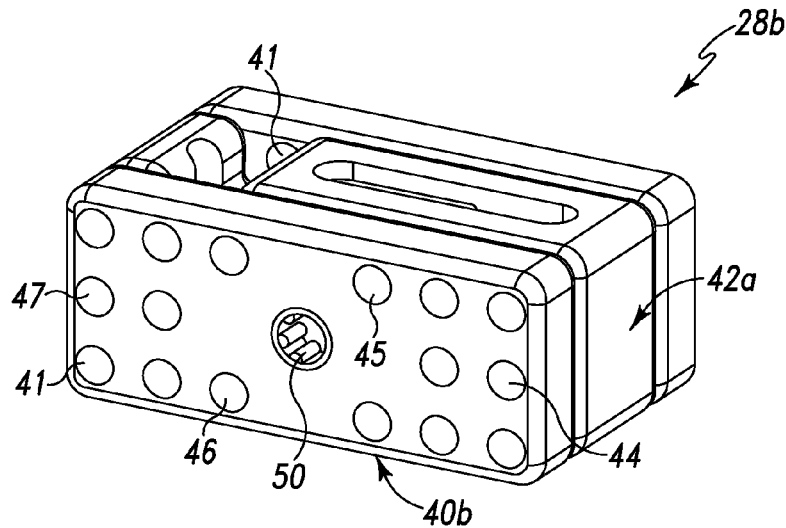
FIG. 4 is a perspective view of an exemplary embodiment of an expandable interbody/intravertebral body device in accordance with the present principles, the expandable interbody/intravertebral body device depicted in a pre-implant or unexpanded state.
Figure 5:
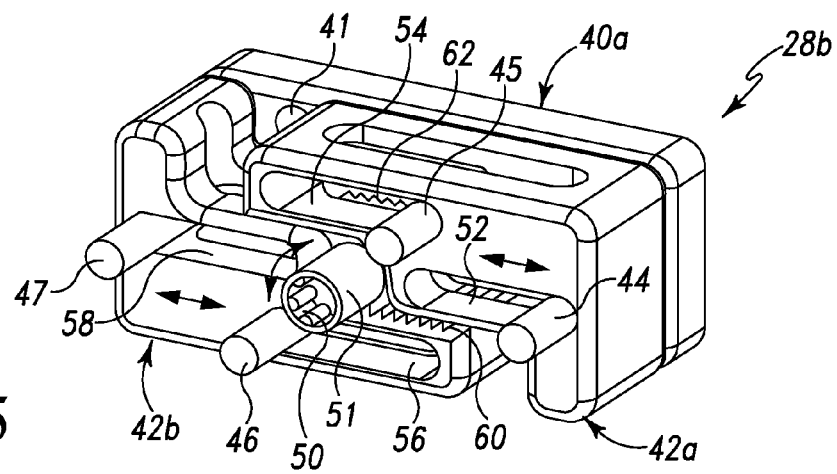
FIG. 5 is a perspective view of the expandable interbody/intravertebral body device of FIG. 4 depicted in the pre-implant or unexpanded state with a plate thereof removed for viewing of an expansion mechanism thereof.
Figure 6:
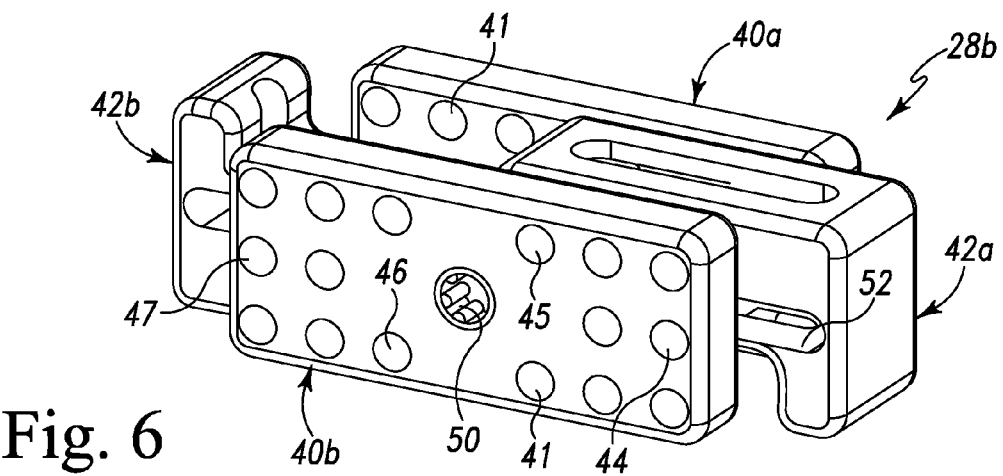
FIG. 6 is a perspective view of the expandable interbody/intravertebral body device of FIG. 4 depicted in a post-implant or expanded state.
Figure 7:
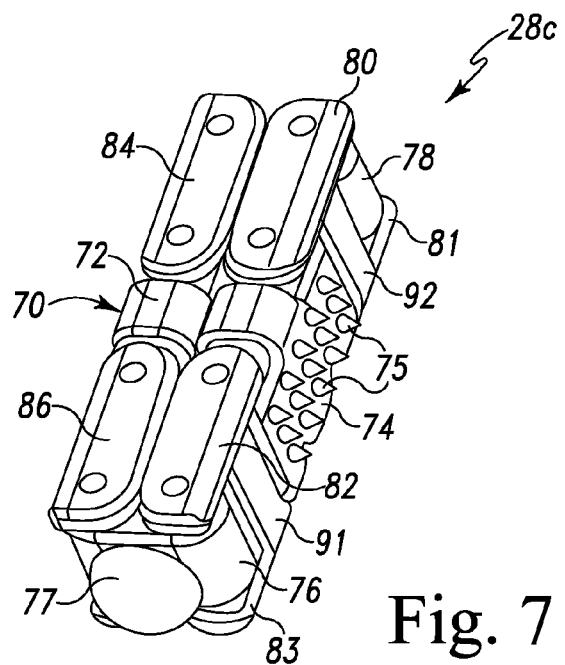
FIG. 7 is a perspective view of an exemplary embodiment of an expandable interbody/intravertebral body device in accordance with the present principles, the interbody/intravertebral body device shown in a pre-implant or unexpanded state.
Figure 9:
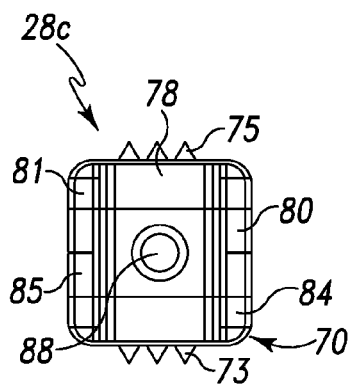
FIG. 9 is a left side view of the expandable interbody/intravertebral body device of FIG. 8 taken along line 9-9 thereof.
Figure 8:
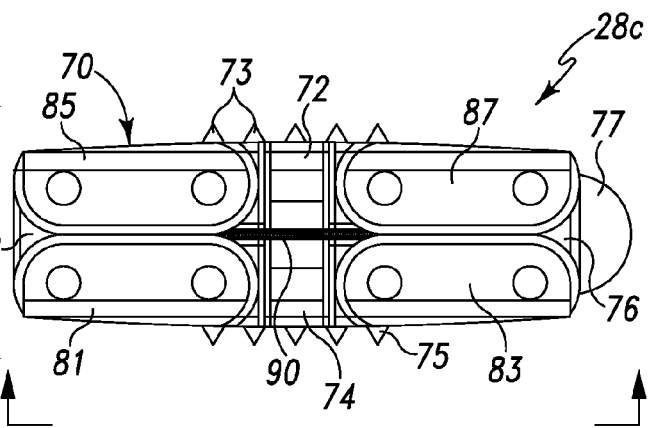
FIG. 8 is a side view of the expandable interbody/intravertebral body device of FIG. 7.
Figure 10:
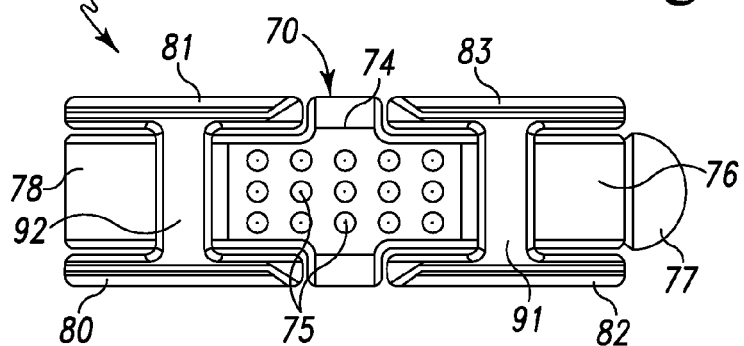
FIG. 10 is a bottom view of the expandable interbody/intravertebral body device of FIG. 8 taken along line 10-10 thereof.

Referring to FIGS. 4-6 there is depicted an embodiment of an expandable and retractable (dynamic) interbody/intravertebral body device generally designated 28b. FIG. 4 depicts the interbody/intravertebral body device 28b in a fully unexpanded or fully retracted position, while FIG. 6 depicts the interbody/intravertebral body device 28b in a fully expanded or fully un-retracted position. Of course, the interbody/intravertebral body device 28b may be positioned anywhere between the fully expanded to fully retracted positions. FIG. 5 depicts the manner in which the interbody/intravertebral body device 28b expands. Thus, in FIG. 5 the end plate 40b is removed for clarity in illustrating such expansion (and oppositely, contraction).

The interbody/intravertebral body device 28b is an anterior inserted interbody/intravertebral body device that provides controlled, horizontal expansion within the intervertebral space 26 as well as vertical retraction within the intervertebral space 26. The interbody/intravertebral body device 28b includes identical end plates 40a, 40b each having holes or bores 41 therein. The end plates 40a, 40b are joined together via posts 44, 45, 46 and 47. The posts 44, 45, 46 and 47 also provide a guide for the identical expansion/retraction members 42a and 42b that are retained between the end plates 40a, 40b.

Particularly, member 42a has a first slot 52 in which post 44 is situated, and a second slot 54 in which post 45 is situated. The slots and posts define the length of travel for the member 42a when the keyed shaft 50 is rotated. As well, the member 42b has a first slot 56 in which post 46 is situated, and a second slot 58 in which post 47 is situated. The slots and posts define the length of travel for the member 42b when the keyed shaft 50 is rotated.

The shaft 50 includes knurls or teeth 51 on an outside thereof that co-act with teeth 60 of member 42a and teeth 62 of the member 42b. Rotation of the shaft 50 in a first radial direction moves the members 42a and 42b in opposite and outward direction. Rotation of the shaft 50 in a second direction (opposite the first direction) moves the members 42a and 42b inwardly.

Referring to FIGS. 7-13 there is depicted another embodiment of an interbody/intravertebral body device generally designated 28c. The interbody/intravertebral body device 28c is shown in a pre-implant or unexpanded/collapsed state in FIGS. 7-10 and in a post-implant or expanded state in FIGS. 11-13. The interbody/intravertebral body device 28c is characterized by a body 70 having a first end plate 72 and a second end plate 75. The first end plate 72 includes a plurality of grips or spikes 73. The second end plate 74 also includes a plurality of grips or spikes 74. The spikes 73, 75 are shown as cone-shaped but may take on other forms. The spikes 73, 75 are designed to grip or extend into adjacent vertebrae.

The interbody/intravertebral body device 28c also includes a first side component 76 and a second side component 78. The first end plate 72 is pivotally connected at one side thereof to the first side component 76 by a first hinge component 93 via hinge plates 86 and 87 of the first hinge component 93, and pivotally connected at another side thereof to the second side component 78 by a second hinge component 94 via hinge plates 84 and 85 of the second hinge component 94. In like manner, the second end plate 74 is pivotally connected at one side thereof to the first side component 76 by a third hinge component 91 via hinge plates 82 and 83 of the third hinge component 91, and pivotally connected at another side thereof to the second side component 78 by a fourth hinge component 92 via hinge plates 80 and 81 of the fourth hinge component 92.

The interbody/intravertebral body device 28c further includes an expansion/contraction member (threaded shaft or screw) 90 that extends through a bore 88 of the second side component 78 and into the head 77 associated with the first side component 76. Expansion of the interbody/intravertebral body device 28c from the collapsed position as depicted in FIGS. 7-10 to the fully expanded position depicted in FIGS. 11-13 is accomplished by pushing the first and second side components 76 and 78 towards each other. As the threaded shaft 90 is rotated, the first and second side components 76, 78 are drawn towards one another. This pivots the first and second end plates 72 and 74 away from each other via the first, second, third and fourth hinge components 93, 94, 91, and 92, respectively.

The interbody/intravertebral body device 28c may be dimensioned as necessary. However, currently it has been found that an optimum implant footprint is approximately 6.35 mm by 9.00 mm. Moreover, the interbody/intravertebral body device 28c is preferably, but not necessarily, dimensioned to have an optimal distraction of 16.00 nm and a maximum distraction of 22.00 mm. As such, the interbody/intravertebral body device 28c is deliverable (implantable) via a minimally invasive tube delivery (e.g. 8 mm tube delivery). Furthermore, the expansion member (e.g. screw) is designed to be a torque limiting break-away screw.

Figure 14:
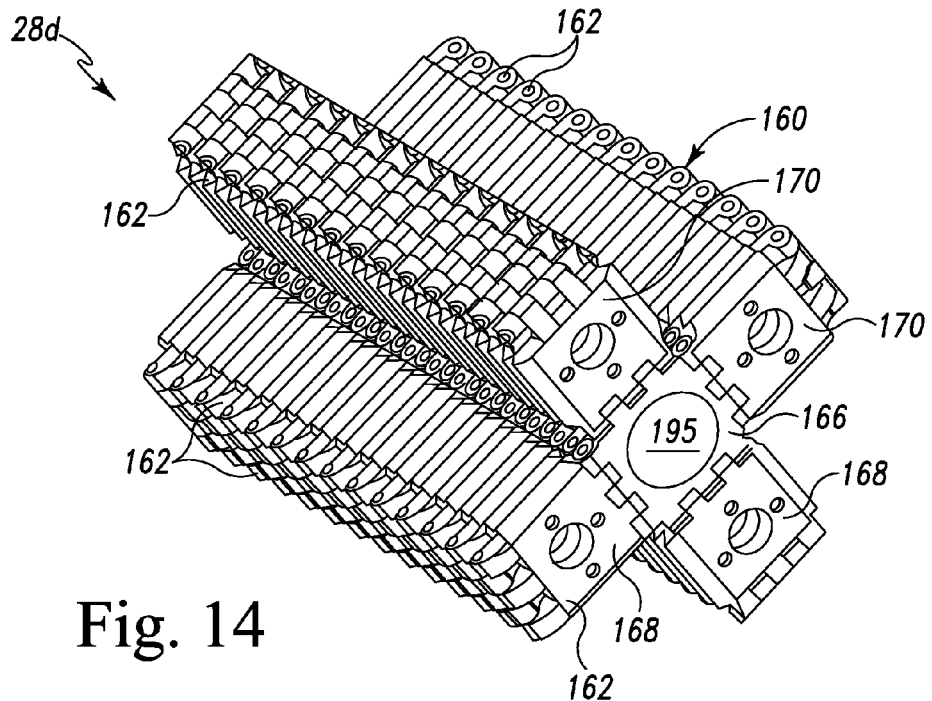
FIG. 14 is front a perspective view of an exemplary embodiment of an expandable interbody/intravertebral body device in accordance with the present principles, the interbody/intravertebral body device shown in a post-implant or expanded state.
Figure 15:
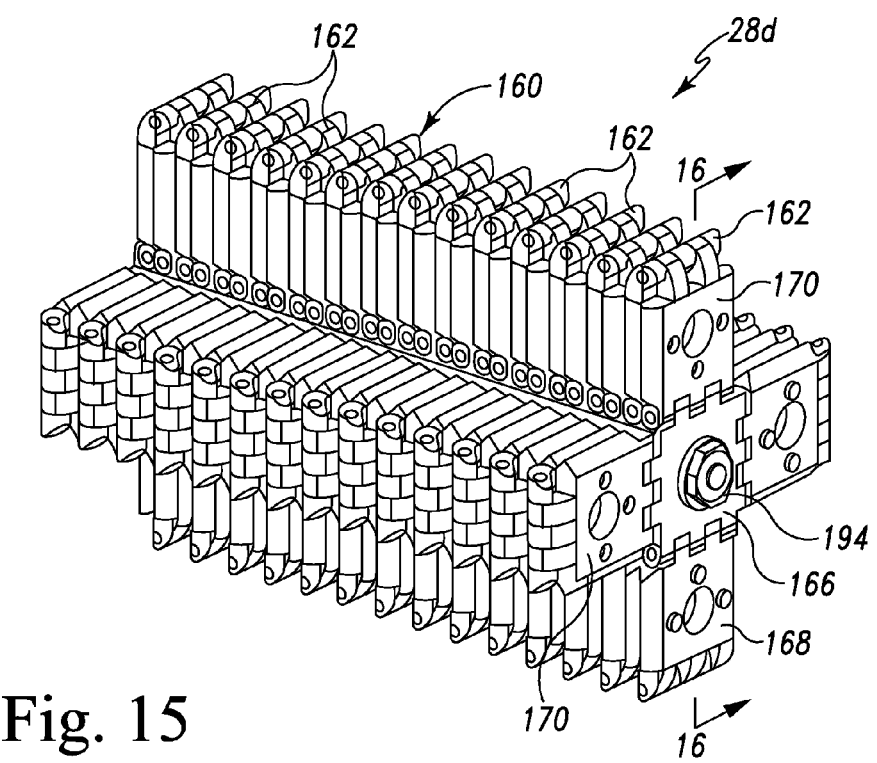
FIG. 15 is a rear perspective view of the expandable interbody/intravertebral body device of FIG. 14.
Figure 17:
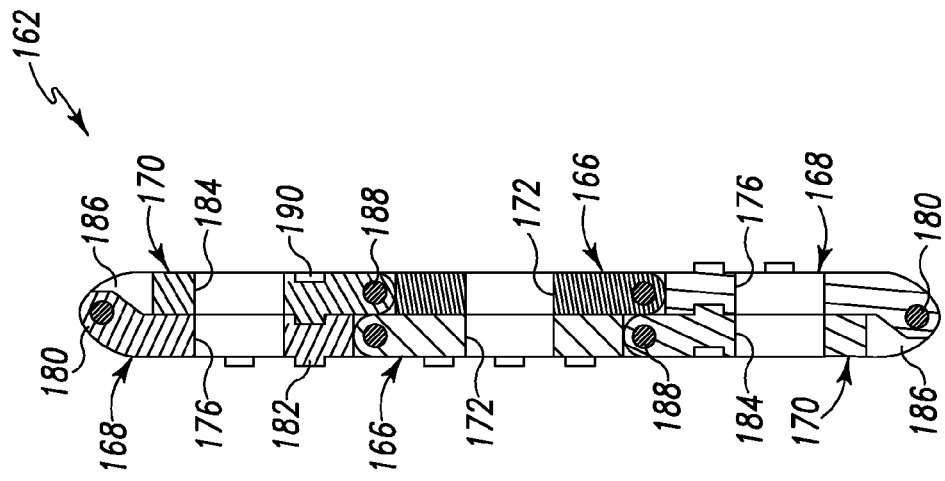
FIG. 17 is an enlarged sectional view of a single segment, section or petal of the expandable interbody/intravertebral body device of FIG. 16, the single segment shown in an expanded position.
Figure 16:
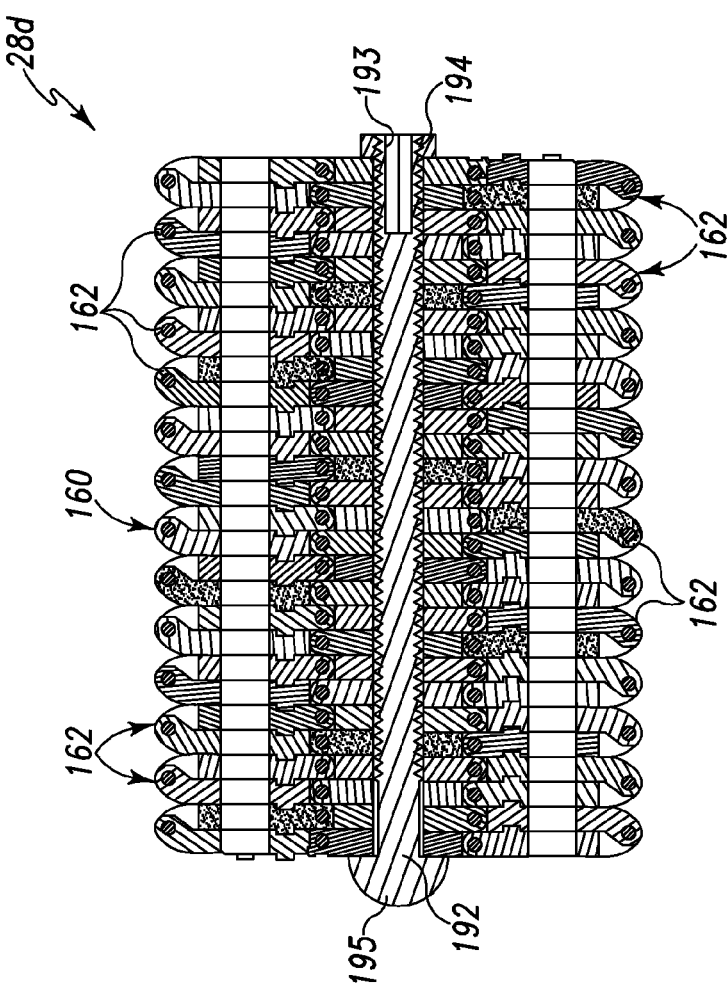
FIG. 16 is a sectional view of the expandable interbody/intravertebral body device of FIG. 15 taken along line 16-16 thereof.
Figure 18:
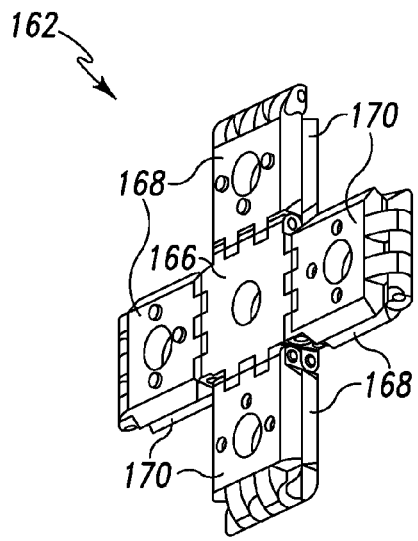
FIG. 18 is a perspective view of the single segment of FIG. 17.
Figure 19:
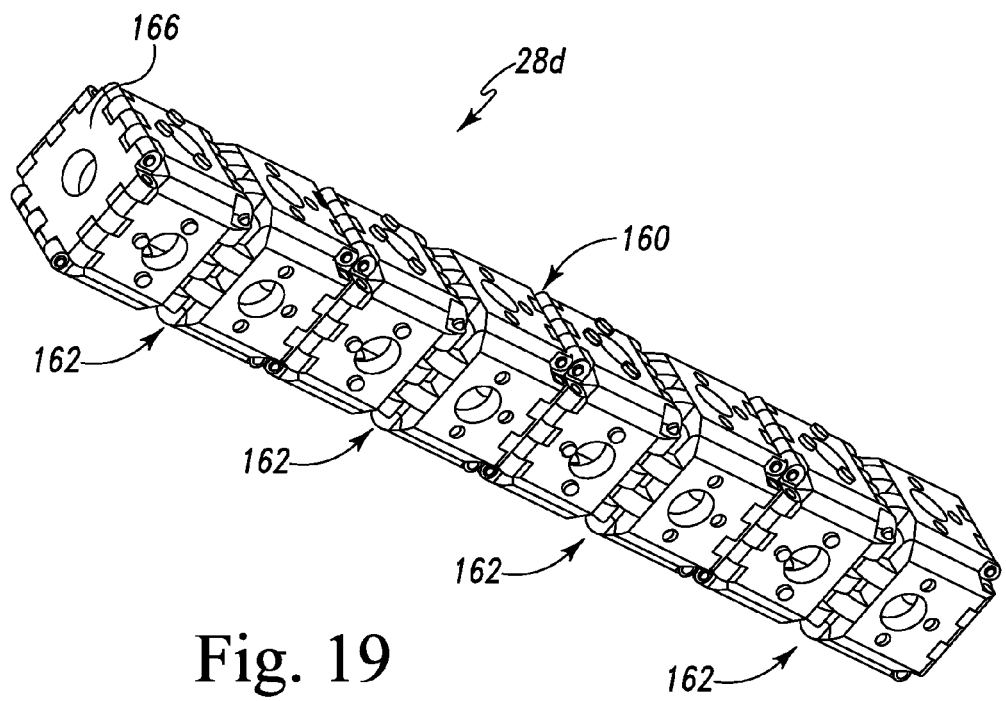
FIG. 19 is a perspective view of a plurality of expandable interbody/intravertebral body segments axially situated one to another forming an implant, the segments shown in a pre-implant or unexpanded state.

Referring to FIGS. 14-22 there is depicted another dynamic interbody/intravertebral body device generally designated 28d. The interbody/intravertebral body device 28d is characterized by a body structure 160 formed by a plurality of dynamic (expands and contracts) sections or portions 162. In FIGS. 14-16, the interbody/intravertebral body device 28d is shown in an expanded or (post) implanted state. In FIG. 19, the interbody/intravertebral body device 28d is shown in a collapsed, folded or pre implant state. In like manner, FIG. 18 depicts one section 162 in an expanded state Each section 162 is formed from three basic plates or components; i.e. an end plate 166 (see FIG. 20) used as a front plate and a back plate, a first inter-connect plate 168 (see FIG. 21) used as type I side plates, and a second inter-connect plate 170 (see FIG. 22) used as type II side plates. The various plates 166, 168 and 170 are pivotally or hingedly coupled to one another to form a section 162 such that the unexpanded box-like structure of each section collapses or folds into an expanded state.

Figure 20:
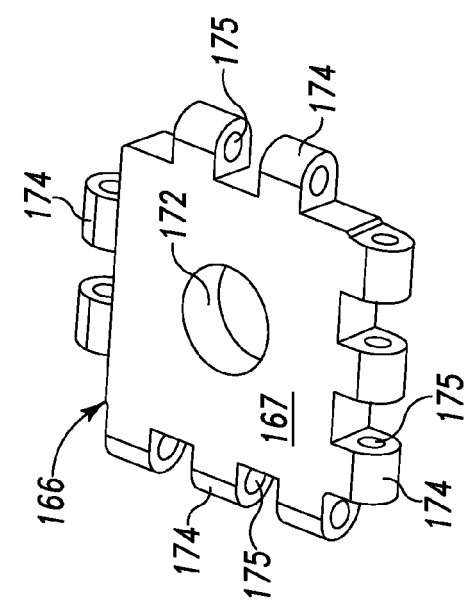
FIG. 20 is an enlarged perspective view of an end plate of the expandable interbody/intravertebral body segment of FIG. 18.

Referring specifically to FIG. 20, end plate 166 is characterized by a rectangular and preferably, but not necessarily, generally square body 167 having a central bore 172. The body 167 includes a plurality of like hinge flanges 174 each having a hinge bore 175 therethrough for receiving a hinge pin. The body 167 includes a first side having three hinge flanges 174, a second side adjacent the first side and having three hinge flanges 174, a third side adjacent the second side (and opposite the first side) and having two hinge flanges 174, and a fourth side adjacent the third and first sides (and opposite the second side) and having two hinge flanges 174.

Figure 21:
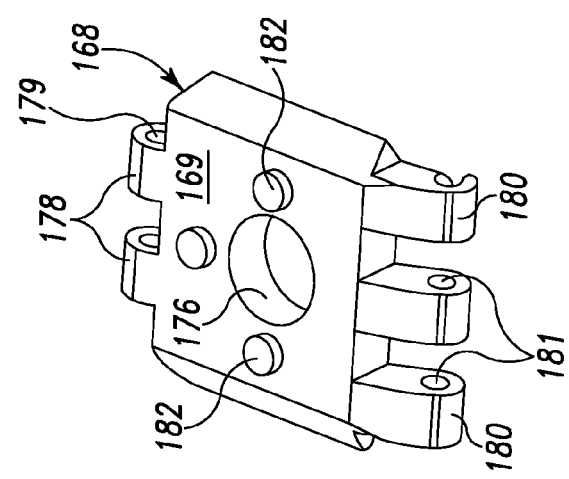
FIG. 21 is an enlarged perspective view of a first interconnect plate of the expandable interbody/intravertebral body segment of FIG. 18.

Referring specifically to FIG. 21, first inter-connect plate 168 is characterized by a rectangular and preferably, but not necessarily, generally square body 169 having a central bore 176. The body 169 includes two hinge flanges 178 of a first configuration each having a hinge bore 179 therethrough for receiving a hinge pin. The two hinge flanges 178 are disposed on one side of the body 169. The body 169 also includes three hinge flanges 180 of a second configuration each having a hinge bore 181 therethrough for receiving a hinge pin disposed on a side of the body 169 opposite the two hinge flange side. Additionally, the body 169 includes a plurality (here shown as three) semi-perf locaters 182 having a raised portion on one side and an indentation on the other side.

Figure 22:
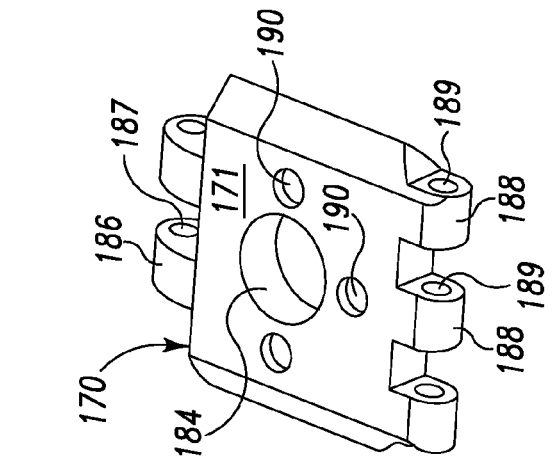
FIG. 22 is an enlarged perspective view of a second interconnect plate of the expandable interbody/intravertebral body segment of FIG. 18.

Referring specifically to FIG. 22 second inter-connect plate 170 is characterized by a rectangular and preferably, but not necessarily, generally square body 171 having a central bore 184. The body 171 includes two hinge flanges 186 of a first configuration each having a hinge bore 187 therethrough for receiving a hinge pin. The two hinge flanges 186 are disposed on one side of the body 171. The body 171 also includes three hinge flanges 188 of a second configuration each having a hinge bore 189 therethrough for receiving a hinge pin disposed on a side of the body 171 opposite the two hinge flange side. Additionally, the body 171 includes a plurality (here shown as three) semi-perf locaters 190 having a raised portion on one side and an indentation (seen in FIG. 22) on the other side. The semi-perf locaters help lock the parts together when the section is expanded. Holes and taper pins may also be used.

The expandable interbody/intravertebral body device 28d may be termed a quad directional interbody/intravertebral body device (e.g. fusion cage) or intervertebral device (e.g. interbody/intravertebral body) that is constructed with interlocking, hinged segments. The expandable interbody/intravertebral body device 28d has an implant footprint (distraction size) of 18.00 mm×18.00 mm (for a size 7 inner segment size). The expandable interbody/intravertebral body device 28d provides push action delivery. A minimally invasive (8 mm) tube delivery may be used. Segments or sections (262) may be added as needed. Preferably, the interbody/intravertebral body device 28d is fashioned from all titanium, but may be fashioned from other biocompatible material. When distracted, there is a 2 mm segment width. The interbody/intravertebral body device 28d may be provided in various sizes ranging from a size 1 through a size 7 with the size 1 having an inner segment size of 4.44 mm and distraction size of 12.00 mm, the size 2 having an inner segment size of 4.81 mm and distraction size of 13.00 mm, the size 3 having an inner segment size of 5.18 mm and distraction size of 14.00 mm, the size 4 having an inner segment size of 5.55 mm and distraction size of 15.00 mm, the size 5 having an inner segment size of 5.92 mm and distraction size of 16.00 mm, the size 6 having an inner segment size of 6.29 mm and distraction size of 17.00 mm, and the size 7 having an inner segment size of 6.66 mm and distraction size of 18.00 mm.

After insertion of the pre-implant structure, a threaded rod 192 having retained the pre-implant structure together during implantation via a head 195, is drawn out by a tool inserted into bore 193 to force the sections 162 to collapse and thus expand. A nut 194 is threadedly received on an exposed end of the rod 192 to retain the body 160 in the expanded state.

Referring to FIGS. 23-51 there is depicted another embodiment of an expandable vertebral interbody/intravertebral body device generally designated 28e. The expandable interbody/intravertebral body device 28e is radially expandable upon axial compression. Radial expansion provides vertical (co-spinal) height within a vertebral body area (see e.g. FIG.

1 area 26). Thus, the interbody/intravertebral body device 28e is characterized by the ability to be inserted or implanted into an open vertebral space in a folded or unexpanded, radially compact state or position and then be unfolded or expanded. The interbody/intravertebral body device 28e is formed of titanium, stainless steel or other biocompatible material, including composites, plastics and/or the like. Radiolucent materials may also be used and, the interbody/intravertebral body device 28e (as well as the other interbody/intravertebral body devices herein) may be formed entirely of a radiolucent material.

Figure 23:
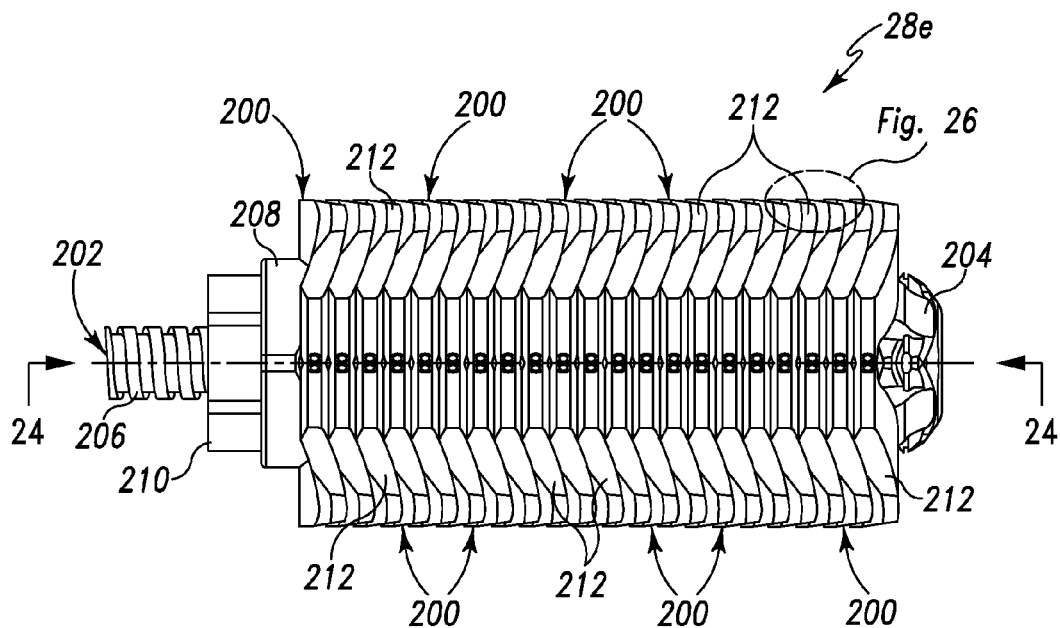
FIG. 23 is a side view of an exemplary embodiment of an expandable interbody/intravertebral body device in accordance with the present principles, the expandable interbody/intravertebral body device shown in a post-implant or expanded state.
Figure 24:
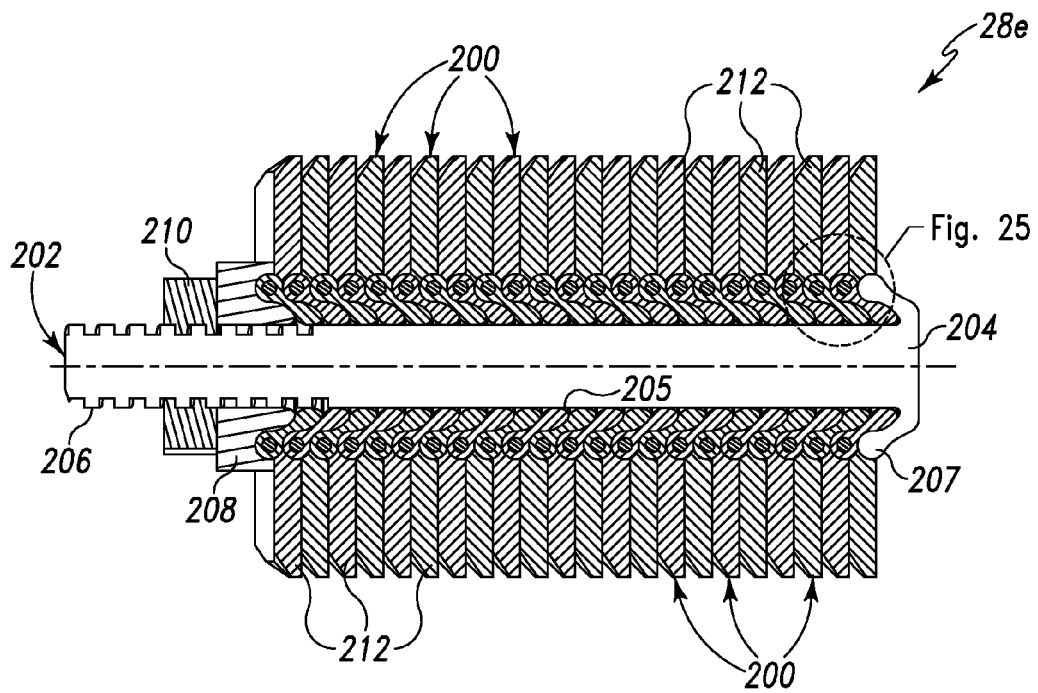
FIG. 24 is a cross-sectional view of the expandable interbody/intravertebral body device of FIG. 23 taken along line 24-24 thereof.
Figure 27:
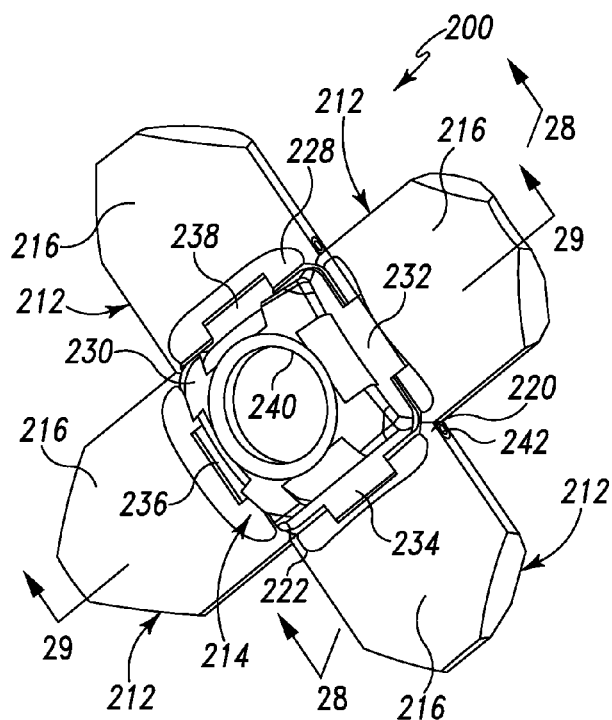
FIG. 27 is an enlarged perspective view of a segment or section of the expandable interbody/intravertebral body device of FIG. 23 in an expanded state.
Figure 30:
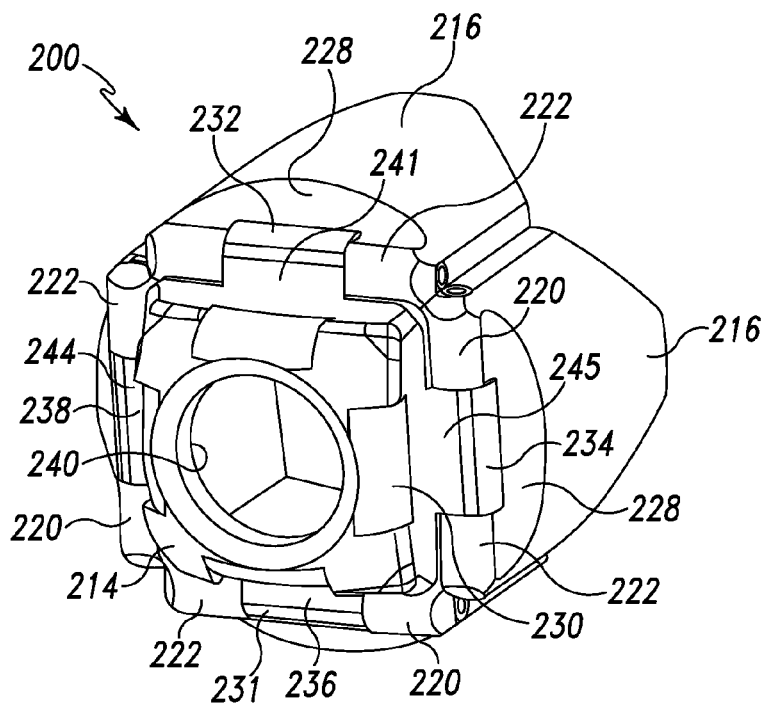
FIG. 30 is an enlarged perspective view of the interbody/intravertebral body segment of FIG. 27 shown in a folded or retracted state.
Figure 46:
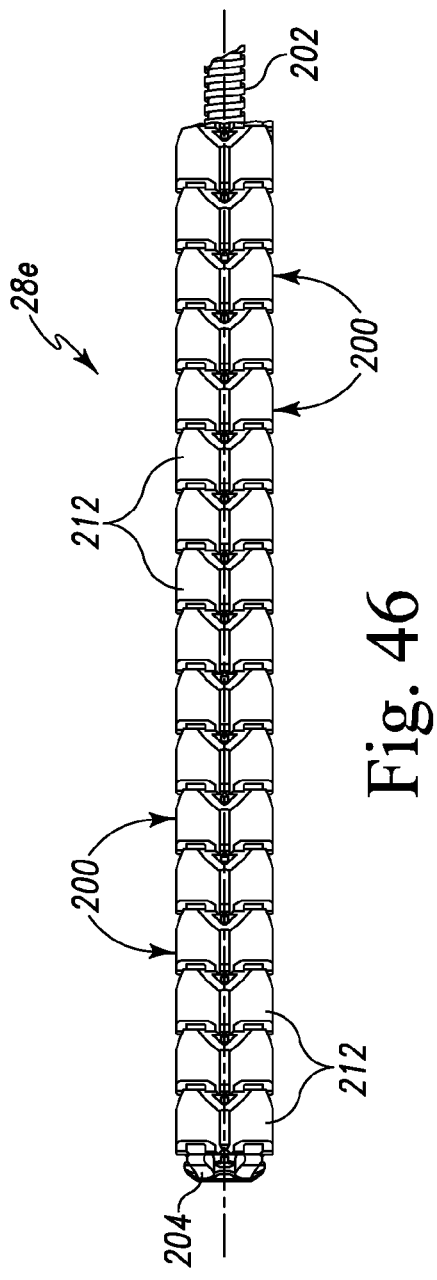
FIG. 46 is a side view of the expandable interbody/intravertebral body device of FIG. 23 in a folded position.

The interbody/intravertebral body device 28e is shown in an expanded position in FIGS. 23 and 24. The interbody/intravertebral body device 28e is characterized by a plurality of segments or sections 200 that each individually expand from a collapsed or unexpanded position into an extended or expanded position to form a vertebral interbody/intravertebral body device. FIG. 46 depicts the interbody/intravertebral body device 28e in a collapsed, folded or pre-deployment position such as after being assembled for introduction or insertion into a vertebral space. FIG. 27 depicts a segment 200 in an expanded or open position such as is seen in FIGS. 23 and 24. FIG. 30 depicts a segment 200 in a collapsed or folded position. The expandable vertebral interbody/intravertebral body device 28e is thus composed of a plurality of segments 200, the number and width thereof defining the overall axial length of the interbody/intravertebral body device 28e when expanded, with the number and axial length of leaves 212 (see, e.g. FIGS. 37-41) of the segments 200 defining the overall radial height of the interbody/intravertebral body device 28e when expanded.

The plurality of segments 200 is carried on an insertion and deployment rod 202. A deploy head or cap 204 is provided at the end of the rod 202 and is preferably integral therewith. The deploy head 204 is configured to engage, cooperate and interact with a central or middle deploy plate 214 of the segment 200. Particularly, a flange structure 207 of the rod 202 engages respective grooves (see FIG. 35 wherein three grooves 241, 244 and 245 of the four grooves of the deploy plate 214 are shown) of the deploy plate 214 (see also FIG. 25). The flange structure 207 represented in FIG. 24 is illustrated in FIGS. 42 and 43. The flange structure of the head 204 consists of four flanges 269, 270, 271 and 272 carried on a rectangular body 266. The four flanges are respectively received in the four grooves of the deploy plate 214. As described further below, axial compression of the deploy plate of the segment and the head of the rod causes the leaves 212 to pivot from an axial position to a position perpendicular to the axial position.

As best seen in FIG. 42, the rod 202 has a threaded shaft portion 206 and a non-threaded shaft portion 205. The non-threaded shaft portion 205 allows the segments 200 to axially slide during expansion of the segments 200. The threaded portion 206 threaded receives the nut 210 allows it to provide the axial force for axial compression of the segments 200 and the expansion thereof.

An end cap 208 is provided on the rod 202 distal from the head 204 of the rod 202 and between the nut 210 and the last (from left to right) deploy plate 214 of the last segment 200. The end cap 208 abuts against the central deploy plate 214 of the last segment 200. The nut 210 abuts the end cap 208. Particularly, the end cap 208 has four grooves 249, 251, 253 and 255 (see FIG. 33) that correspond to the four tubular flanges or hinge structures (which will be referred to as tubular hinge structures 232, 234, 236 and 238) of the central deploy plate 214. The tubular hinge structures of the deploy plate 214 are nested or received into the grooves of the end plate 208. Moreover, a threaded nut 210 is provided on the rod 202 to provide axial compression of the segments 200 when threadedly advanced toward the head 204 of the rod 202 to achieve radial expansion of the interbody/intravertebral body device 28e. This is done after proper placement of the interbody/intravertebral body device 28e into a vertebral space 26.

As seen in FIGS. 33 and 34, the end cap 208 is particularly characterized by a body 246 having a central or middle bore 247 that is sized to be received onto the rod 202. The body 246 defines four flanges 248, 250, 252 and 254 on sides thereof. The four flanges 248, 250, 252 and 254 each defining a respective groove 249, 251, 253 and 255 and a respective contact surface 262, 256, 260 and 258. The grooves 249, 251, 253 and 255 providing a contact surface for the tubular hinge structures 232, 234, 236 and 238 of the deploy plate 214.

Figure 26:
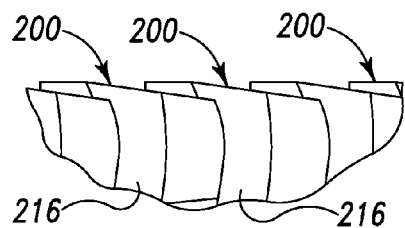
FIG. 26 is an enlarged portion of the side view of the expandable interbody/intravertebral body device of FIG. 23.
Figure 25:
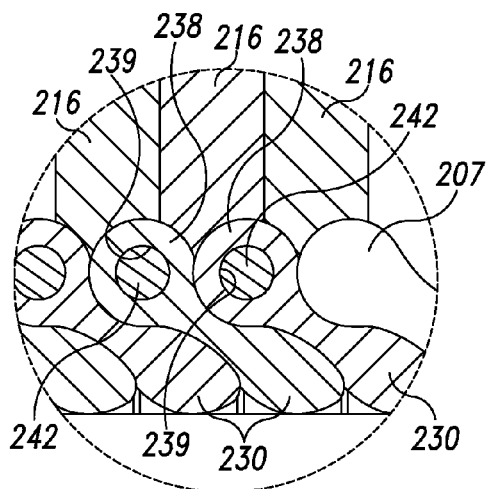
FIG. 25 is an enlarged portion of the sectional view of the expandable interbody/intravertebral body device of FIG. 24.
Figure 28:
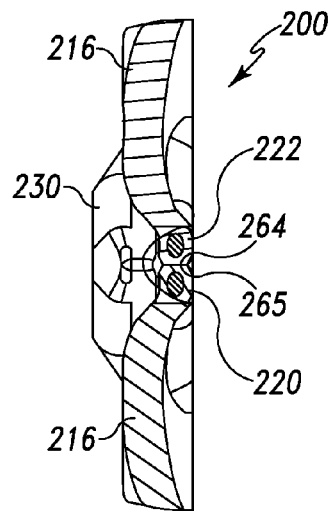
FIG. 28 is a sectional view of the interbody/intravertebral body segment of FIG. 27 taken along line 28-28 thereof.
Figure 29:
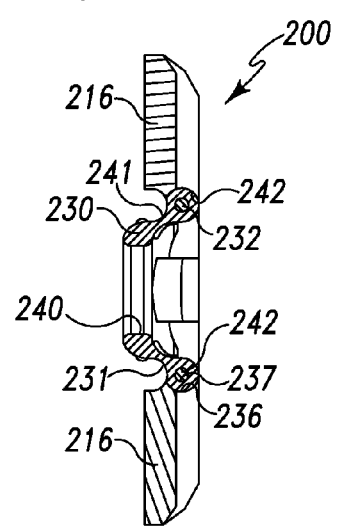
FIG. 29 is a sectional view of the interbody/intravertebral body segment of FIG. 28 taken along line 29-29 thereof.
Figure 31:
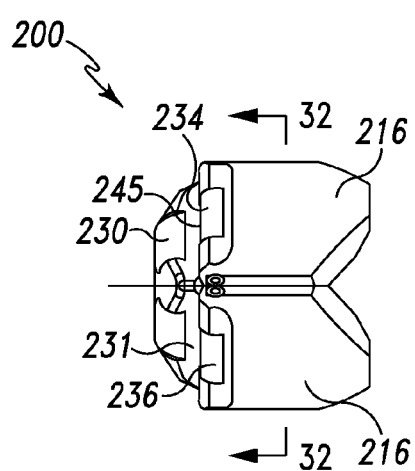
FIG. 31 is a side view of the folded interbody/intravertebral body segment.
Figure 32:
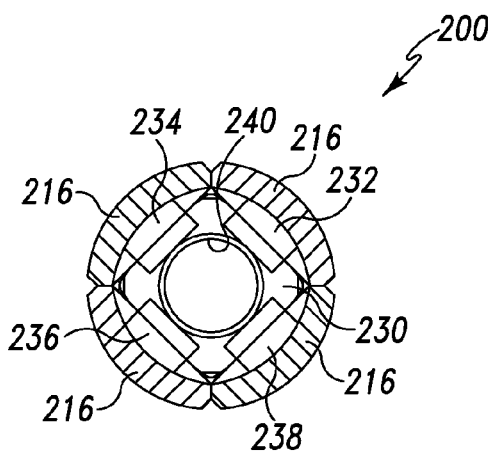
FIG. 32 is a sectional view of the folded interbody/intravertebral body segment of FIG. 31 taken along line 31-31 thereof.
Figure 37:
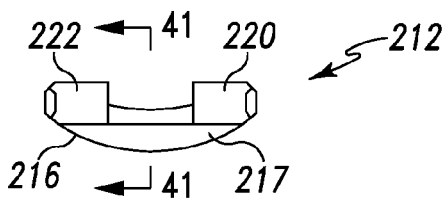
FIG. 37 is a front view of a leaf of the interbody/intravertebral body segment.
Figure 38:
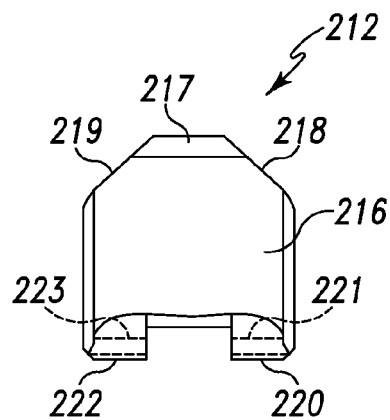
FIG. 38 is a bottom view of the leaf of the interbody/intravertebral body segment.
Figure 39:
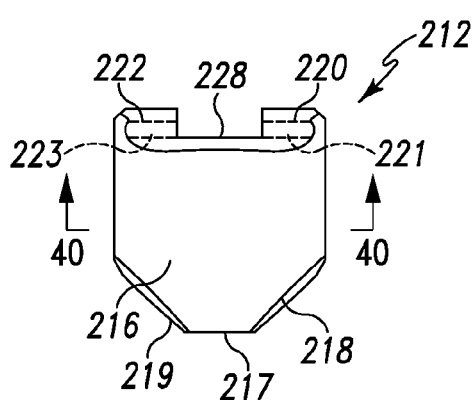
FIG. 39 is a top view of the leaf of the interbody/intravertebral body segment.
Figure 40:
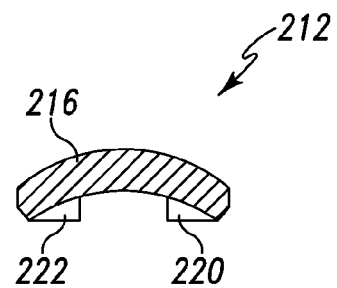
FIG. 40 is a sectional view of the leaf of the interbody/intravertebral body segment taken along line 40-40 of FIG. 39.
Figure 41:
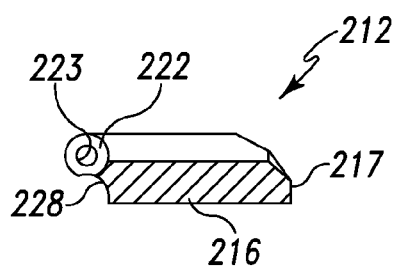
FIG. 41 is a sectional view of the leaf of the interbody/intravertebral body segment taken along line 41-41 of FIG. 37.

As seen in FIGS. 27-32, the segments 200 include the middle or central deploy plate 214 (see FIG. 33) to which are pivotally, hingedly or swingably attached a plurality (here, four) leaf structures 212. The leaf structures 212 are pivotally attached to the deploy plate 214 by hinge pins 242 and are structured to provide a collapsed or folded position as seen in FIGS. 30-32 wherein a longitudinal axis of each leaf structure 212 is essentially co-axial with the rod 202, and an expanded or open position as seen in FIGS. 27-29 where the longitudinal axis of each leaf structure 212 is essentially perpendicular to the longitudinal axis of the rod 202. The folded position of the segments 200 provide a small diameter device, while the expanded position of the segments 200 provides a larger diameter device constrained by the length of the leaf structures 212. As illustrated in FIG. 26, the leaf bodies 216 of the segments 200 form a toothed, stepped or jagged profile.

Referring to FIGS. 35 and 36, the deploy plate 214 of a segment 200 is particularly shown. The deploy plate 214 is characterized by a generally rectangular body 230 having a central or middle bore 240. The bore 240 is sized to be received onto the rod 202. Four cylindrical or tubular flanges 232, 234, 236 and 238 extend from the four sides of the body 230. Each tubular flange 232, 234, 236 and 238 has a bore 233, 235, 237 and 239 respectively for receipt of a pivot pin 242. The body 230 also defines four grooves 241, 245, 231, and 244 adjacent the four flanges 232, 234, 236 and 238 respectively.

Referring to FIGS. 37-41 the leaf structure 212 of a segment 200 is particularly shown. A leaf structure 212 consists of a leaf body 216 having a generally "home-plate" shape (see e.g., FIGS. 38, 39) with an arched profile (see e.g., FIGS. 37, 40). As such, the body 216 includes a front 217 and two angled portions 218, 219. First and second tubular or cylindrical pivot flanges 220, 222 are provided on one side 228 of the body 216. The first flange 220 includes a bore 221 for receipt of the pivot pin 242. The second flange 222 includes a bore 223 for receipt of a pivot pin 242. The two flanges 220 and 222 are spaced from one another so as to receive a tubular flange (e.g., flange 232) of the deploy plate body 230 such that the two flanges 220, 222 of the leaf body 216 straddle or are on opposite axial sides of the respective deploy plate tubular flange. In this manner a pivot pin 242 may extend through the flange 220 of the leaf body 216, the tubular flange of the deploy plate body 230, and through the flange 222 of the leaf body 216. When four leaf structures 212 are connected to the middle body 230, the leaf bodies 216 can pivot between a closed, folded or collapsed position (FIG. 30) and an open, extended or expanded position (FIG. 27).

As best seen in FIG. 28, when the leaf structures 212 are expanded, the rounded flanges 220 and 222 and flats 264 and 265 on ends of the flanges 220 and 222 of the leaf body 216 coact to provide a positive or snap feature to lock the leaf structures 212 in the expanded postion.

The interbody/intravertebral body/intervertebral body device 28e, like the other interbody/intravertebral body device described herein, are designed to be delivered, installed, implanted or positioned in a patient via a cannula or tube. Such a cannula 274 is illustrated in FIGS. 44 and 45. The cannula 274 is defined by a tubular body 276 having an inner or inside surface 278. Four prongs or protrusions 280, 281, 282 and 283 are provided on the inside surface 278. These serve to guide, orient and allow expansion of the interbody/intravertebral body device 28 during implantation.

Figure 47:
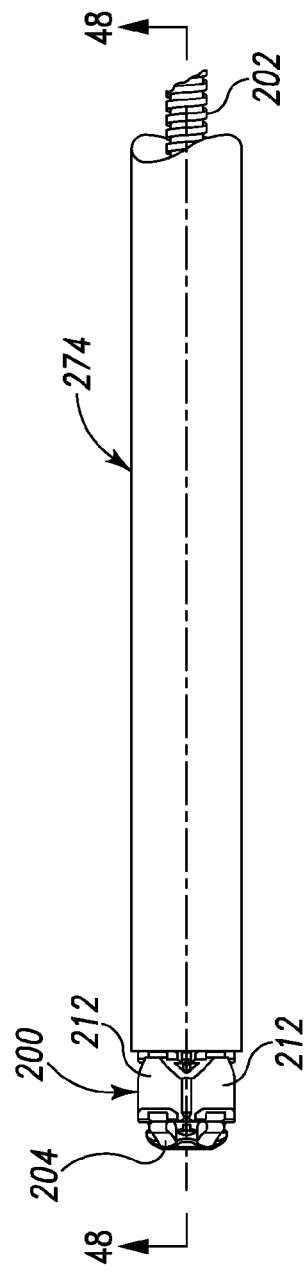
FIG. 47 is a side view of the insertion and deployment cannula of FIG. 45 holding the folded interbody/intravertebral body device of FIG. 46.

FIGS. 46-49 provide an illustration of the interbody/intravertebral body device 28e assembled for being implanted in a vertebral space. FIG. 46 shows an interbody/intravertebral body device 28e assembled and in a collapsed position. The number of segments 200 determines the overall axial length of the resulting expanded device. The assembled and collapsed interbody/intravertebral body device is provided in the cannula 274 in FIG. 47. A sectional view of FIG. 47 is provided in FIG. 48. FIG. 49 particularly depicts the juncture of the end of the cannula 274 and a segment 200 of the interbody/intravertebral body device 28e. At this point, a first segment may be deployed (expanded).

Figure 51:
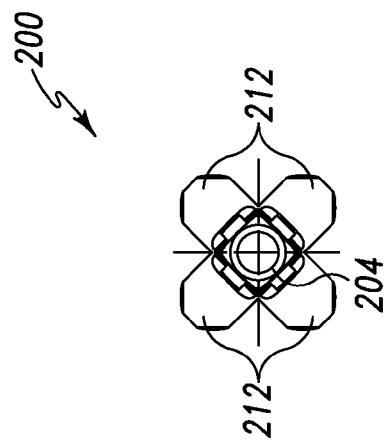
FIG. 51 is an end view of the interbody/intravertebral body device of FIG. 50 taken along line 51-51 thereof.
Figure 50:
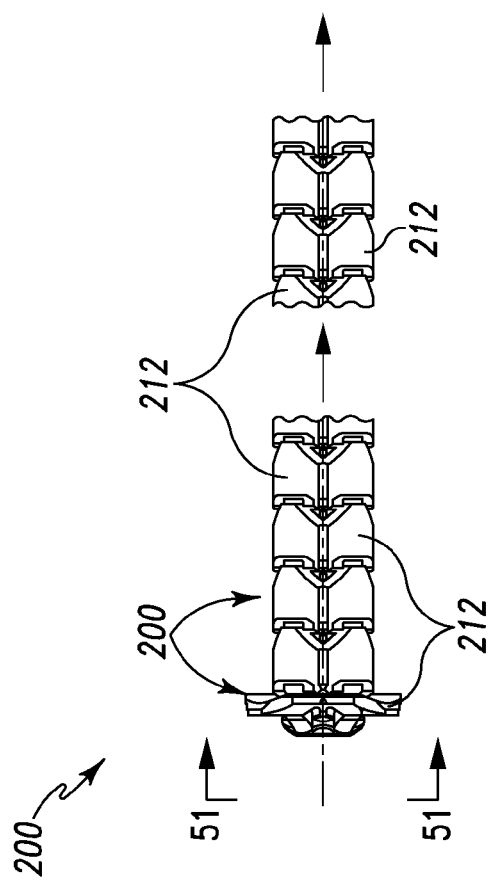
FIG. 50 is a side view of the folded expandable interbody/intravertebral body device of FIG. 46 illustrating deployment thereof.

FIGS. 50 and 51 particularly illustrate how axial compression (represented by the arrows) causes the segments 200 to expand. Particularly, axially compression causes a first segment 200 to expand. Thereafter, each successive segment expands in a somewhat "domino" effect as more axial compression is applied. In this embodiment, axial compression is provided by the nut 210. Thus, when the interbody/intravertebral body device 28e is properly placed, the nut 210 is rotated to provide axial compression until all of the segments 200 are expanded.

Figure 52:
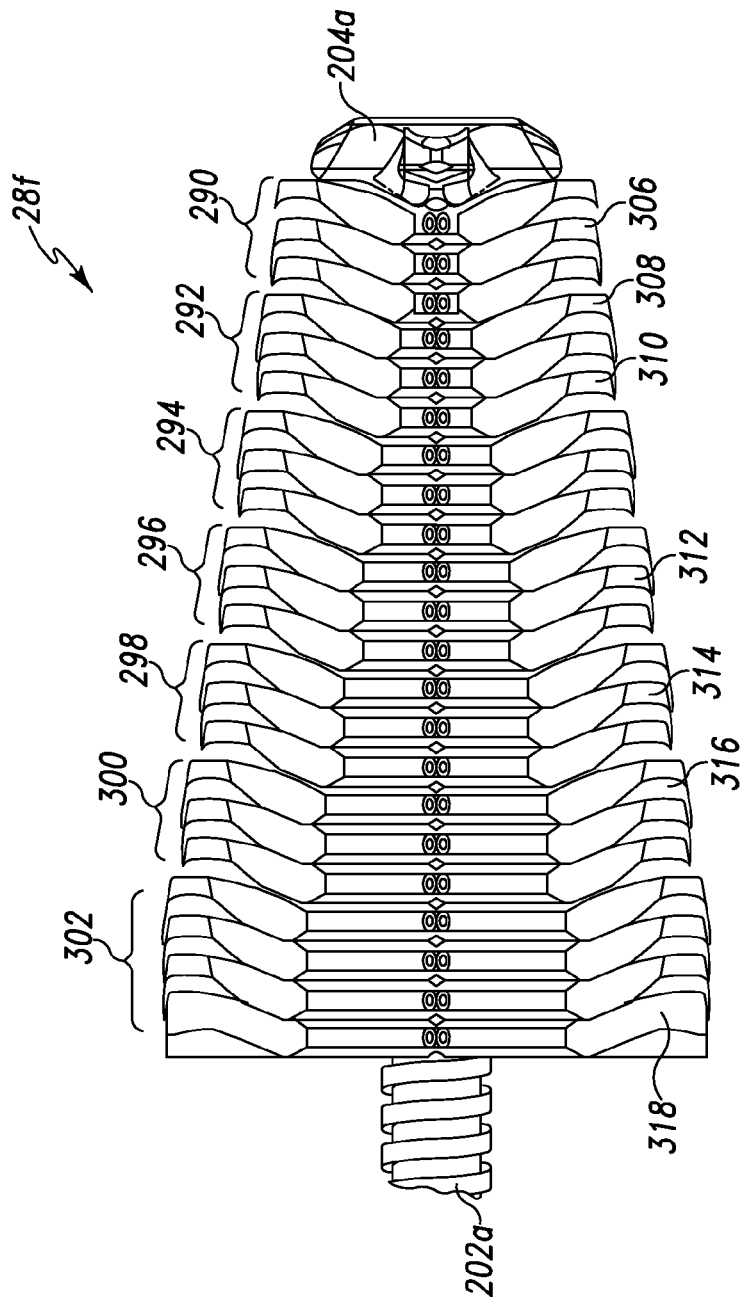
FIG. 52 is a perspective view of an exemplary embodiment of an expandable interbody/intravertebral body device in accordance with the present principles, the interbody/intravertebral body device shown in a post-implant or expanded position.
Figure 53:
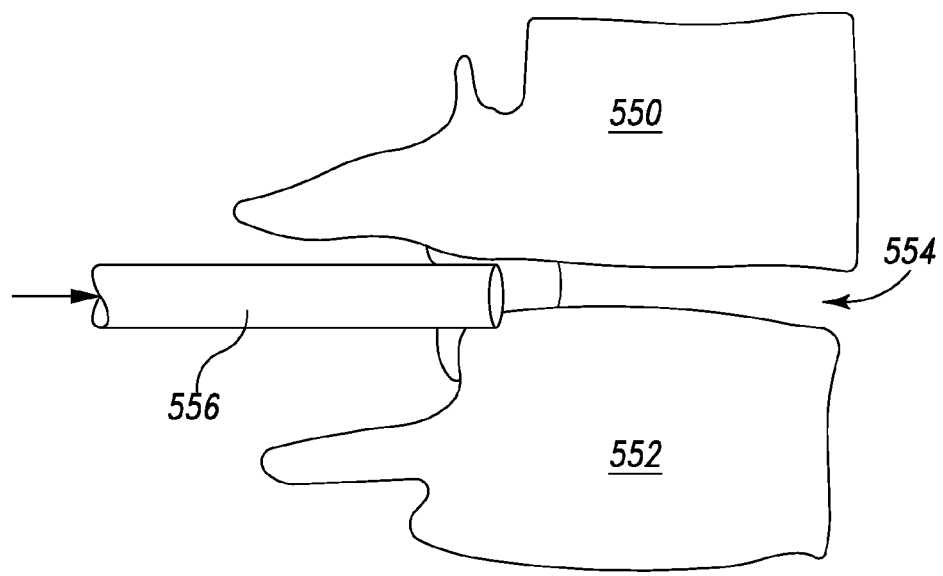
FIG. 53 is a side view of adjacent vertebrae with a cannula (insertion and deployment tube) used to introduce or implant an expandable interbody/intravertebral body device as provided herein.
Figure 54:
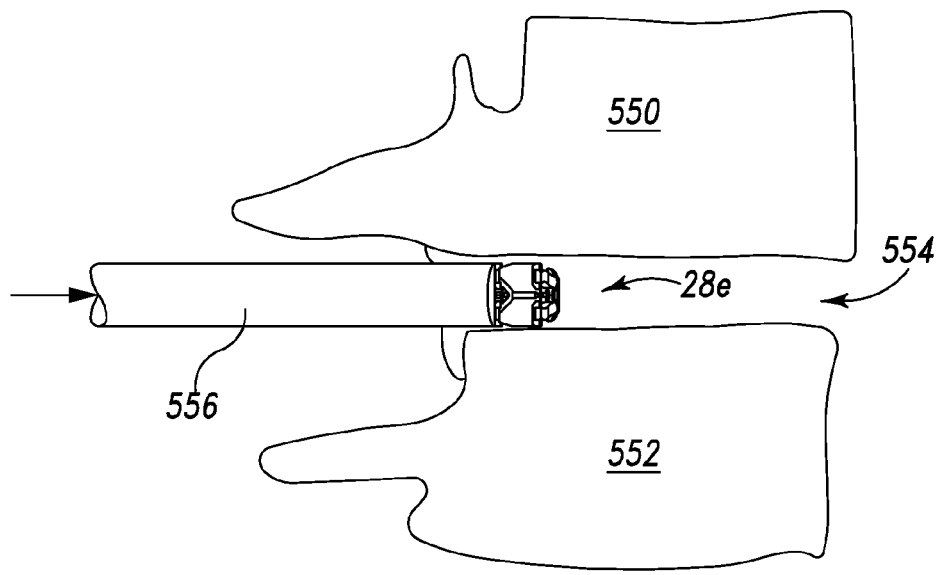
FIG. 54 is the view of FIG. 63 wherein an expandable interbody/intravertebral body device is being inserted between vertebrae.

FIG. 52 depicts an alternative embodiment or variation of the interbody/intravertebral body device 28e illustrating how different radial profiles may be created by using segments of various sizes (dimensions). In FIG. 52 there is depicted a frusto-conically shaped interbody/intravertebral body device generally designated 28f. The interbody/intravertebral body device 28f is shown in a post-implant or expanded state. The interbody/intravertebral body device 28f includes a plurality 290, 292, 294, 296, 298, 300 and 302 of groups of interbody/intravertebral body segments each group of segments 290, 292, 294, 296, 298, 300 and 302 having respective leaves 306, 308, 310, 312, 314, 316 and 318 of different radial height. As can be appreciated, the axial length of any group 290, 292, 294, 296, 298, 300 and 302 is determined by the number of segments in the group. The radial height or profile of each group 290, 292, 294, 296, 298, 300 and 302 is determined by the radial height of the leaf structures (and the middle plate) of the segments. A multitude of radial profiles may be created.

It should be appreciated that the segments 200 of the various interbody/intravertebral body devices may or may not be at least limitedly movable relative to one another. In one case, the segments 200 are fixed relative to each other and therefore no movement can occur between the segments. In another case, the segments 200 are at least limitedly movable radially with respect to another segment 200 such that the interbody/intravertebral body is dynamic. This allows for limited movement within the interbody/intravertebral body device itself.

Figure 55:
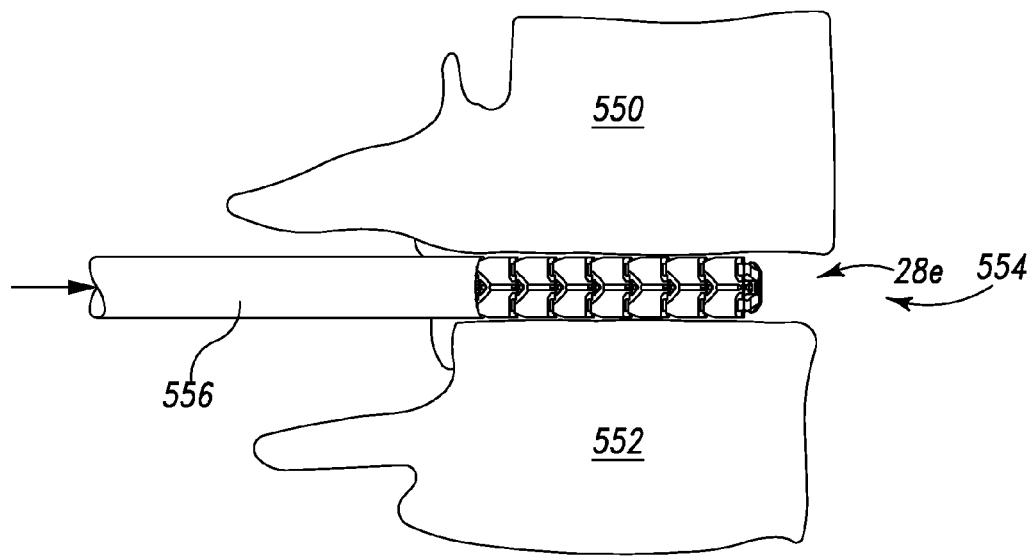
FIG. 55 is the view of FIG. 63 wherein the expandable interbody/intravertebral body device has been properly positioned for expansion/deployment.
Figure 56:
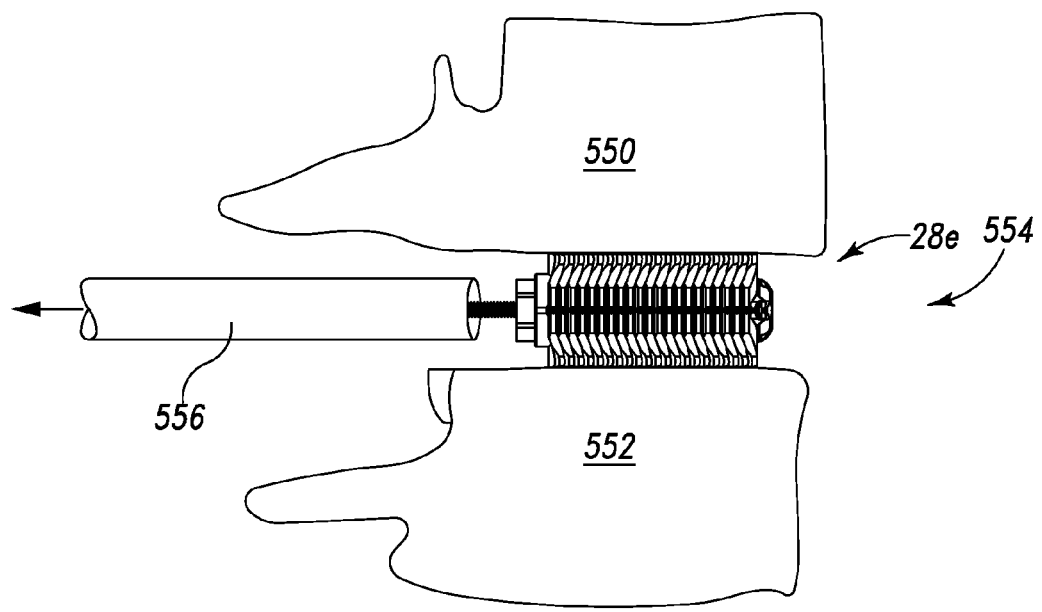
FIG. 56 is the view of FIG. 63 wherein the expandable interbody/intravertebral body device has been fully expanded or deployed.

Referring lastly to FIGS. 53-56, there is illustrated a manner of implanting the interbody/intravertebral body devices 28a-28f. Particularly, but without restriction or being necessarily so, the various interbody/intravertebral body devices 28a-28f are percutaneously implanted via a cannula 556. The end of the cannula 556 is positioned proximate an intervertebral space 554 between a first vertebra 550 and a second vertebra 552. The particular interbody/intravertebral body device (here, interbody/intravertebral body device 28e is shown) is then inserted into the cannula 556 as represented by the arrow. Once the particular interbody/intravertebral body device is appropriately placed in the intervertebral space 554, the interbody/intravertebral body device is expanded via an appropriate instrument through the cannula 556. As shown in FIG. 55 the interbody/intravertebral body device 28e is received in the vertebral space 554. In FIG. 56, the interbody/intravertebral body device 28e has been radially expanded to vertically fill the vertebral space 554 through axial compression of the segments 200 of the interbody/intravertebral body device 28e.

Figure 57:
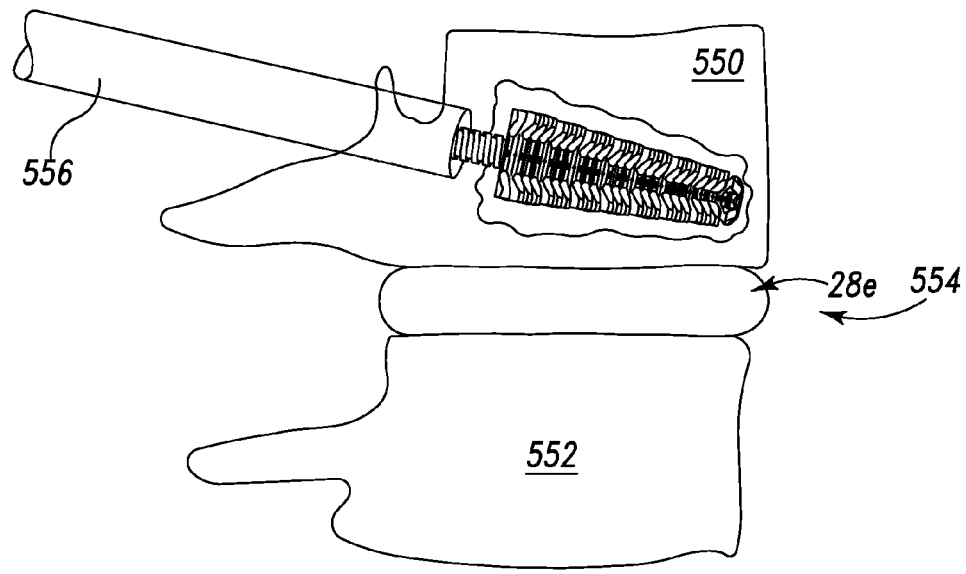
FIG. 57 is side view of a portion of a spinal column showing two adjacent vertebrae with a cannula (insertion and deployment tube) used to introduce or implant an expandable interbody/intravertebral body device as an intravertebral body device, the expandable intravertebral body device shown in an unexpanded position.
Figure 58:
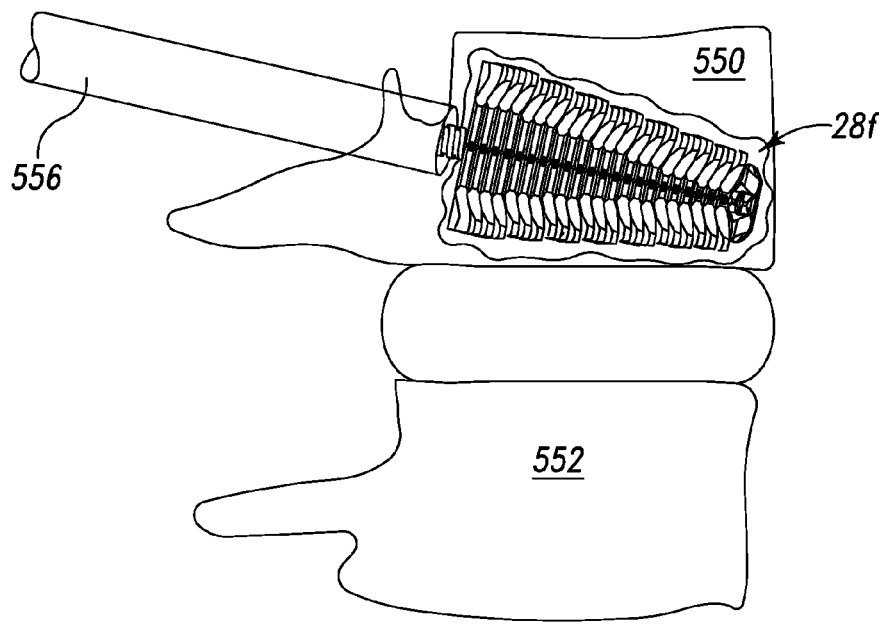
FIG. 58 is the view of FIG. 57 wherein the expandable intravertebral device is shown in an expanded position within the vertebra.

FIGS. 57 and 58 illustrate use of a spinal body 28 as an intravertebral body device. Particularly interbody/intravertebral body 28f is shown in FIG. 57 as implanted via cannula 556 into vertebra 550 (intravertebral). The intravertebral device 28f is initially unexpanded. In FIG. 58, the intravertebral device 28f has been expanded within the vertebra. This use is applicable to treat vertebral compression fractures and/or the like.

It should be appreciated that each interbody/intravertebral body device 28a through 28e may be scaled to any size necessary. Additionally, each interbody/intravertebral body device 28a-28e is manufactured from a bio-compatible material such as a titanium-based metal. Variations are also contemplated.

What is claimed is:

1. An implant for insertion into a spinal space, the implant comprising:
    a deployment component; and
    a plurality of segments disposed on the deployment component, each one of the plurality of segments is radially expandable from a first outer dimension to a second outer dimension that is greater than the first outer dimension upon axial compression of the plurality of segments relative to the deployment component, the plurality of segments includes at least a first segment and a second segment;
    wherein each of the plurality of segments includes a pivoting plate that pivots in the same direction as the associated pivoting plate on the adjacent segment, and includes an inner surface and an outer surface;
    wherein the first segment at least partially nests within the second segment upon axial compression of the plurality of segments so that the outer surface of the first segment at least partially faces the inner surface of the second segment.

2. The implant of claim 1, wherein each one of the plurality of segments includes a plurality of pivoting plates.

3. The implant of claim 1, wherein each one of the plurality of segments comprises one to four pivoting plates.

4. The implant of claim 1, wherein each one of the plurality of segments includes at least one pivoting plate.

5. The implant of claim 2, wherein the plurality of pivoting plates deploys along an arc.

6. The implant of claim 2, wherein the plurality of pivoting plates provides a receptacle for bone, bone material, bone growth material, medicaments, or therapeutics.

7. The implant of claim 2, wherein the plurality of pivoting plates is pivotally disposed about a deployment plate that is disposed on the deployment component.

8. The implant of claim 7, wherein pivotal positions of the plates defines the first outer dimension and the second outer dimension, and wherein in the first outer dimension, each one of the plurality of pivoting plates is positioned such that its longitudinal axis is co-axial with a longitudinal axis of the deployment component, and in the second outer dimension, the plurality of pivoting plates is positioned such that its longitudinal axis is (at least or on an angle from zero to 90 degrees) perpendicular to the longitudinal axis of the deployment component.

9. The implant of claim 1, wherein the deployment component comprises a rod, the rod having a head abutting a first segment of the plurality of segments and a threaded portion for receipt of a compression component, wherein axial compression is applied to the plurality of segments through the compression component.

10. The implant of claim 9, further comprising an end cap situated between a last segment of the plurality of segments and the compression component.

11. The implant of claim 1, wherein the plurality of segments is composed of a radiolucent material.

12. The implant of claim 1, wherein the deployment component and the plurality of segments are composed of a radiolucent material.

13. The implant of claim 1, wherein at least one of the plurality of segments is radially movable relative to others of the plurality of segments.

14. The implant of claim 1, wherein the plurality of segments is radially movable relative to one another.

15. The implant of claim 1, wherein the plurality of segments is radially fixed relative to one another.

16. A spinal body for intravertebral/intervertebral implantation, the spinal body comprising:
a deployment component; and
a plurality of expansion structures carried on the deployment component;
wherein the plurality of expansion structures define a first axial length and a first radial dimension when the expansion structures are in a collapsed position;
wherein when the expansion structures are in an expanded position due to axial compression of the plurality of expansion structures, the plurality of expansion structures: define a second axial length that is less than the first axial length, have a second radial dimension that is greater than the first radial dimension, and are at least partially nested into one another.

17. The spinal body of claim 16, wherein each one of the plurality of expansion structures includes a plurality of pivoting plates each one of which is pivotable along an arc into the collapsed position and the expanded position.

18. The spinal body of claim 17, wherein the plurality of expansion structures include at least a first expansion structure and a second expansion structure, wherein the arcs of pivoting plates on the first expansion structure are parallel and axially offset from the arcs of the comparable pivoting plates on the second expansion structure.

19. The spinal body of claim 17, wherein the plurality of pivoting plates is pivotally disposed about a deployment plate that is disposed on the deployment component.

20. The spinal body of claim 16, wherein each one of the plurality of expansion structures comprises one to four pivoting plates.

21. The spinal body of claim 20, wherein the pivoting plates provides a receptacle for bone, bone material, bone growth material, medicaments, or therapeutics.

22. The spinal body of claim 17, wherein the pivoting plates snap lock into the expanded position.

23. The spinal body device of claim 16, wherein the deployment component comprises a rod, the rod having a head abutting a first segment of the plurality of expansion structures and a threaded portion for receipt of a compression component, wherein axial compression applied to the expansion structures through the compression component changes the collapsed position of the expansion structures into the expanded position of the expansion structures.

24. The spinal body of claim 23, further comprising an end cap situated between a last structure of the plurality of structures and the compression component.

25. The spinal body of claim 16, wherein the plurality of structures is composed of a radiolucent material.

26. The spinal body of claim 16, wherein at least one of the plurality of structures is radially movable relative to others of the plurality of structures.

27. The spinal body of claim 16 wherein the plurality of structures is radially movable relative to one another.

28. The spinal body of claim 16, wherein the plurality of structures is radially fixed relative to one another.

29. A method of introducing a spinal body into an intervertebral or intravertebral space, the method comprising the steps of:
providing an implant comprising a deployment component and a plurality of segments disposed on the deployment component wherein each one of the plurality of segments is radially expandable from a first outer dimension to a second outer dimension that is greater than the first outer dimension upon axial compression of the plurality of segments relative to the deployment component, the plurality of segments includes at least a first segment and a second segment, and wherein each of the plurality of segments includes a pivoting plate that pivots in the same direction as the associated pivoting plate on the adjacent segment and includes an inner surface and an outer surface, the implant initially having the first outer dimension, wherein the first segment at least partially nests within the second segment upon axial compression of the plurality of segments so that the outer surface of the first segment at least partially faces the inner surface of the second segment;
inserting the implant of the first outer dimension into a cannula;
positioning an opening of the cannula adjacent the vertebral space;
extending the implant of the first outer dimension out of the cannula and into the vertebral space; and
providing axial compression to the implant to put the implant into the second outer dimension by pivoting the pivoting plates in the same direction as the associated pivoting plate on the adjacent segment.

30. The method of claim 29, wherein the plurality of pivoting plates are pivotally disposed about a deployment plate of the segment, and the deployment plate is disposed on the deployment component.

31. The method of claim 29, wherein pivotal positions of the plates defines the first outer dimension and the second outer dimension, and wherein in the first outer dimension, each one of the plurality of pivoting plates is positioned such that its longitudinal axis is co-axial with a longitudinal axis of the deployment component, and in the second outer dimension, the plurality of pivoting plates is positioned such that its longitudinal axis is perpendicular to the longitudinal axis of the deployment component.

32. The method of claim 29, wherein the deployment component comprises a rod, the rod having a head abutting the first segment of the plurality of segments and a threaded portion for receipt of a compression component, wherein axial compression is applied to the plurality of segments through the compression component.

* * * * *